United States Patent
Uchiyama et al.

(10) Patent No.: US 10,168,339 B2
(45) Date of Patent: Jan. 1, 2019

(54) MARKER PEPTIDE FOR DETERMINING RISK OF DEVELOPING METABOLIC SYNDROME, AND USE THEREOF

(71) Applicant: LION CORPORATION, Tokyo (JP)

(72) Inventors: Chiyoko Uchiyama, Tokyo (JP); Kei Kurita, Tokyo (JP); Eriko Fukushima, Tokyo (JP); Riichi Maki, Tokyo (JP)

(73) Assignee: LION CORPORATION, Tokyo (JP)

( * ) Notice: Subject to any disclaimer, the term of this patent is extended or adjusted under 35 U.S.C. 154(b) by 919 days.

(21) Appl. No.: 14/371,655

(22) PCT Filed: Dec. 27, 2012

(86) PCT No.: PCT/JP2012/083889
§ 371 (c)(1),
(2) Date: Jul. 10, 2014

(87) PCT Pub. No.: WO2013/108561
PCT Pub. Date: Jul. 25, 2013

(65) Prior Publication Data
US 2015/0160239 A1    Jun. 11, 2015

(30) Foreign Application Priority Data
Jan. 16, 2012 (JP) .................. 2012-006354

(51) Int. Cl.
| | |
|---|---|
| C07K 14/575 | (2006.01) |
| C07K 14/705 | (2006.01) |
| C07K 16/26 | (2006.01) |
| C07K 16/28 | (2006.01) |
| C12M 1/34 | (2006.01) |
| G01N 27/62 | (2006.01) |
| G01N 37/00 | (2006.01) |
| G01N 33/68 | (2006.01) |
| C07K 14/72 | (2006.01) |
| C07K 14/47 | (2006.01) |
| G01N 33/543 | (2006.01) |
| C07K 14/435 | (2006.01) |

(52) U.S. Cl.
CPC ....... *G01N 33/6893* (2013.01); *C07K 14/435* (2013.01); *C07K 14/47* (2013.01); *C07K 14/723* (2013.01); *G01N 33/54366* (2013.01); *G01N 2333/435* (2013.01); *G01N 2800/04* (2013.01); *G01N 2800/50* (2013.01)

(58) Field of Classification Search
None
See application file for complete search history.

(56) References Cited

U.S. PATENT DOCUMENTS

| | | |
|---|---|---|
| 2007/0281306 A1 | 12/2007 | Hodge et al. |
| 2009/0042208 A1 | 2/2009 | Davies et al. |
| 2009/0226450 A1 | 9/2009 | Hodge et al. |
| 2010/0015146 A1* | 1/2010 | Lau ............... C07K 14/7155 424/136.1 |
| 2010/0331278 A1* | 12/2010 | Anderson ............. A23L 2/52 514/57 |
| 2011/0124022 A1 | 5/2011 | Nagalla et al. |
| 2011/0171205 A1 | 7/2011 | Hodge et al. |
| 2012/0087862 A1 | 4/2012 | Hood et al. |
| 2014/0106981 A1 | 4/2014 | Hood et al. |

FOREIGN PATENT DOCUMENTS

| | | |
|---|---|---|
| JP | 2004-194534 A | 7/2004 |
| JP | 2005-137202 A | 6/2005 |
| JP | 2009-145220 A | 7/2009 |
| WO | WO 02/079780 A1 | 10/2002 |
| WO | WO 2008/021290 A2 | 2/2008 |
| WO | WO 2010/011860 A1 | 1/2010 |

OTHER PUBLICATIONS

Isemura et al., "Isolation and amino acid sequences of proline-rich peptides of human whole saliva." J. Biochem. 86:79-86(1979).*
Ramasubbu et al, "Large-scale purification and characterization of the major RT phosphoproteins and mucins of human submandibular-sublingual saliva." Biochem. J. 280:341-352(1991).*
International Search Report dated Mar. 26, 2014 in PCT/JP2012/083889.
Eva J. Helmerhorst, et al., "Identification of Lys-Pro-Gln as a novel cleavage site specificity of saliva-association proteases", The Journal of Biological Chemistry, vol. 283, No. 29, Jul. 18, 2008, pp. 19957-19966.

(Continued)

*Primary Examiner* — Julie Ha
*Assistant Examiner* — Kristina M Hellman
(74) *Attorney, Agent, or Firm* — Oblon, McClelland, Maier & Neustadt, L.L.P.

(57) ABSTRACT

It is an object of the present invention to provide a marker substance capable of accurately determining a risk of developing metabolic syndrome in vivo. That is, the present invention provides the followings: a marker peptide for determining the risk of developing the metabolic syndrome; an antibody or an aptamer bound to the marker peptide for determining the risk of developing the metabolic syndrome; a microarray in which the antibody or the aptamer bound to the marker peptide for determining the risk of developing the metabolic syndrome has been immobilized on a carrier; a method for determining the risk of developing the metabolic syndrome, comprising measuring an amount or the presence or absence of the marker peptide for determining the risk of developing the metabolic syndrome in a biological sample collected from a subject; and a kit for determining the risk of developing the metabolic syndrome, comprising the antibody or the aptamer or comprising the microarray.

10 Claims, 6 Drawing Sheets

Specification includes a Sequence Listing.

(56) References Cited

OTHER PUBLICATIONS

Seiki Ito, et al, "A study on salivary peptide P-C with special reference to intracellular localization of salivary peptide P-C like immunoreactivity in the human pancreatic B-cells", Folia Endocrinologica Japonica, vol. 60, No. 9, 1984, pp. 1080-1090 (with English Abstract).
Brian B. Haab, "Applications of the antibody array platforms", Current Opinion in Biotechnology, vol. 17, 2006, pp. 415-421.
Edited by Nikkei Biotechnology, Himan/Metabolic Syndrome, Nikkei Bio Nenkan 2012 Kenkyu Kaihatsu to Shijo Sangyo Doko, Dec. 13, 2011, pp. 167-169 and Cover Page (with English language translation).
Toshio Morizane,"Wakariyasui Igaku Tokeigaku", 1$^{st}$ Edition, Oct. 1, 2004, pp. 148-179 and Cover Page (with English language translation).
Francisco Amado, et al., "Salivary peptidomics", Expert Review of Proteomics, vol. 7, No. 5, 2010, pp. 709-721.
Francis C. Lynn, et al., "A novel pathway for regulation of glucose-dependent insulinotropic polypeptide (GIP) receptor expression in beta cells", FASEB Journal, vol. 17, No. 1, 2003, pp. 91-93.
Tiziana Cabras, et al., "Alterations of the salivary secretory peptidome profile in children affected by type 1 diabetes", Molecular & Cellular Proteomics, vol. 9, No. 10, Oct. 2010, pp. 2099-2108.
Richa Saxena, et al., "Genetic variation in GIPR influences the glucose and insulin response to an oral glucose challenge", Nature Gen., vol. 42, No. 2, Feb. 2010, 16 Pages.
U.S. Appl. No. 14/438,479, filed Apr. 24, 2015, Uchiyama, et al.
Extended European Search Report dated Jul. 6, 2015 in Patent Application No. 12866020.6.
Satoko Isemura, "Nucleotide Sequence of Gene PBII Encoding Salivary Proline-Rich Protein P-B$^1$", Journal of Biochemistry, vol. 127, No. 3, (Mar. 1, 2000), pp. 393-398.
Richa Saxena ,et al., "Genetic variation in GIPR influences the glucose and insulin responses to an oral glucose challenge", Nature Genetics, vol. 42, No. 2, (Feb. 1, 2010), pp. 142-148.
Massimo Castagnola, et al., "Biotechnological implications of the salivary proteome", Trends in Biotechnology, vol. 29, No. 8, pp. 409-418.
Paturi V. Rao, et al., "Proteomic Identification of Salivary Biomarkers of Type-2 Diabetes", Journal of Proteome Research, vol. 8, No. 1, XP009122608, (Jan. 2, 2009), pp. 239-245.
Rosanna Inzitari, et al., "Detection in human saliva of different statherin an P-B fragments and derivatives", Proteomics, vol. 6, No. 23, (Dec. 1, 2006), pp. 6370-6379.
Chin J. Diabetes, China Academic Journal Electronic Publishing House, vol. 13, No. 3, Jun. 2005, pp. 178-180.
"Gastric inhibitory polypeptide receptor [*Homo sapiens*]" NCBI Accession #: NP_000155 [https://www.ncbi.nlm.nih.gov/protein/4503999?sat=88.satkey=496924], Mar. 19, 1999, 1 Page.
Office Action as received in the corresponding Chinese Patent Application No. 201610116241 dated Jul. 24, 2018 w/English Translation.
Yin Chang-Sheng, et al., "The expression of GIPR in vasculature endothelial cell in transplanted islets", China Excellent Master's Thesis full Text Database, Journal of Chongqing Medical University 2010, vol. 35, No. 1, Feb. 15, 2008, pp. 1-53.

\* cited by examiner

<P-B PEPTIDE FRAGMENT (2)$^{23\text{-}54}$ COMPARISON OF SIGNALS>

<P-B PEPTIDE FRAGMENT $(3)^{55-79}$ COMPARISON OF SIGNALS>

<P-B PEPTIDE FRAGMENT $(4)^{23-79}$ COMPARISON OF SIGNALS>

<P-B PEPTIDE FRAGMENT $(5)^{23\text{-}35}$ COMPARISON OF SIGNALS>

```
                        SEQUENCE LISTING

<160> NUMBER OF SEQ ID NOS: 2

<210> SEQ ID NO 1
<211> LENGTH: 79
<212> TYPE: PRT
<213> ORGANISM: Homo sapiens

<400> SEQUENCE: 1

Met Lys Ser Leu Thr Trp Ile Leu Gly Leu Trp Ala Leu Ala Ala Cys
1               5                   10                  15

Phe Thr Pro Gly Glu Ser Gln Arg Gly Pro Arg Gly Pro Tyr Pro Pro
            20                  25                  30

Gly Pro Leu Ala Pro Pro Gln Pro Phe Gly Pro Gly Phe Val Pro Pro
```

```
                35                  40                  45
Pro Pro Pro Pro Pro Tyr Gly Pro Gly Arg Ile Pro Pro Pro Pro
            50                  55                  60

Ala Pro Tyr Gly Pro Gly Ile Phe Pro Pro Pro Pro Gln Pro
65                  70                  75
```

<210> SEQ ID NO 2
<211> LENGTH: 466
<212> TYPE: PRT
<213> ORGANISM: Homo sapiens

<400> SEQUENCE: 2

```
Met Thr Thr Ser Pro Ile Leu Gln Leu Leu Arg Leu Ser Leu Cys
1               5                   10                  15

Gly Leu Leu Leu Gln Arg Ala Glu Thr Gly Ser Lys Gly Gln Thr Ala
                20                  25                  30

Gly Glu Leu Tyr Gln Arg Trp Glu Arg Tyr Arg Arg Glu Cys Gln Glu
            35                  40                  45

Thr Leu Ala Ala Ala Glu Pro Pro Ser Gly Leu Ala Cys Asn Gly Ser
        50                  55                  60

Phe Asp Met Tyr Val Cys Trp Asp Tyr Ala Ala Pro Asn Ala Thr Ala
65                  70                  75                  80

Arg Ala Ser Cys Pro Trp Tyr Leu Pro Trp His His His Val Ala Ala
                85                  90                  95

Gly Phe Val Leu Arg Gln Cys Gly Ser Asp Gly Gln Trp Gly Leu Trp
            100                 105                 110

Arg Asp His Thr Gln Cys Glu Asn Pro Glu Lys Asn Glu Ala Phe Leu
        115                 120                 125

Asp Gln Arg Leu Ile Leu Glu Arg Leu Gln Val Met Tyr Thr Val Gly
        130                 135                 140

Tyr Ser Leu Ser Leu Ala Thr Leu Leu Leu Ala Leu Leu Ile Leu Ser
145                 150                 155                 160

Leu Phe Arg Arg Leu His Cys Thr Arg Asn Tyr Ile His Ile Asn Leu
                165                 170                 175

Phe Thr Ser Phe Met Leu Arg Ala Ala Ala Ile Leu Ser Arg Asp Arg
            180                 185                 190

Leu Leu Pro Arg Pro Gly Pro Tyr Leu Gly Asp Gln Ala Leu Ala Leu
        195                 200                 205

Trp Asn Gln Ala Leu Ala Ala Cys Arg Thr Ala Gln Ile Val Thr Gln
        210                 215                 220

Tyr Cys Val Gly Ala Asn Tyr Thr Trp Leu Leu Val Glu Gly Val Tyr
225                 230                 235                 240

Leu His Ser Leu Leu Val Leu Val Gly Gly Ser Glu Glu Gly His Phe
                245                 250                 255

Arg Tyr Tyr Leu Leu Leu Gly Trp Gly Ala Pro Ala Leu Phe Val Ile
            260                 265                 270

Pro Trp Val Ile Val Arg Tyr Leu Tyr Glu Asn Thr Gln Cys Trp Glu
        275                 280                 285

Arg Asn Glu Val Lys Ala Ile Trp Trp Ile Ile Arg Thr Pro Ile Leu
        290                 295                 300

Met Thr Ile Leu Ile Asn Phe Leu Ile Phe Ile Arg Ile Leu Gly Ile
305                 310                 315                 320

Leu Leu Ser Lys Leu Arg Thr Arg Gln Met Arg Cys Arg Asp Tyr Arg
                325                 330                 335
```

```
Leu Arg Leu Ala Arg Ser Thr Leu Thr Leu Val Pro Leu Leu Gly Val
            340             345             350

His Glu Val Val Phe Ala Pro Val Thr Glu Glu Gln Ala Arg Gly Ala
            355             360             365

Leu Arg Phe Ala Lys Leu Gly Phe Glu Ile Phe Leu Ser Ser Phe Gln
        370             375             380

Gly Phe Leu Val Ser Val Leu Tyr Cys Phe Ile Asn Lys Glu Val Gln
385             390             395             400

Ser Glu Ile Arg Arg Gly Trp His His Cys Arg Leu Arg Arg Ser Leu
                405             410             415

Gly Glu Glu Gln Arg Gln Leu Pro Glu Arg Ala Phe Arg Ala Leu Pro
            420             425             430

Ser Gly Ser Gly Pro Gly Glu Val Pro Thr Ser Arg Gly Leu Ser Ser
            435             440             445

Gly Thr Leu Pro Gly Pro Gly Asn Glu Ala Ser Arg Glu Leu Glu Ser
            450             455             460

Tyr Cys
465
```

MARKER PEPTIDE FOR DETERMINING RISK OF DEVELOPING METABOLIC SYNDROME, AND USE THEREOF

TECHNICAL FIELD

The present invention relates to a marker peptide for determining a risk of developing metabolic syndrome, and use thereof.

BACKGROUND ART

The number of patients with metabolic syndrome has currently increased, and is described to reach 20 million including the number of those having a risk of developing the metabolic syndrome in Japan. The metabolic syndrome in severe cases causes arterial sclerosis, resulting in myocardial infarction or cerebral infarction, and thus its early detection and prevention are important. A specific medical checkup (checkup for metabolic syndrome) was made obligatory for the purpose of its early detection in April, 2008. Preventive measures for the metabolic syndrome may include food intake, and functional foods including foods for specified health use have been marketed for preventing obesity and/or the metabolic syndrome.

On the other hand, various marker substances that are included in living bodies and are indicators for diagnosis of diseases have been reported. For example, it has been described in Non-patent Literature 1 that a level of a P-B peptide that is a proline-rich peptide in saliva is significantly reduced in patients with pediatric type I diabetes. It has been also described in Non-patent Literature 2 that polymorphism of a GIPR gene is correlated to a blood glucose level 2 hours after a glucose tolerance test.

CITATION LIST

Non-Patent Literatures

Non-patent Literature 1: Mol. Cell Proteomics, October 2010; 9 (10): 2099-108.
Non-patent Literature 2: Nature Genet., February 2010: 42(2): 142-148.

SUMMARY OF INVENTION

Problem to be Solved by the Invention

However, functional foods have been problematic in that its preventive effect on metabolic syndrome is difficult to be realized and consumers are difficult to keep motivation for continuously using these foods. No marker substance capable of becoming an indicator for the metabolic syndrome has been found so far.

It is an object of the present invention to provide a marker substance for accurately determining a risk of developing the metabolic syndrome in the body.

Means for Solving Problem

As a result of an extensive study, the present inventors have found that parts of amino acid sequences of a P-B peptide and GIPR are useful as marker peptides for determining a risk of developing metabolic syndrome and the risk of developing the metabolic syndrome can be determined by determining an amount of the marker peptide in a biological sample such as saliva. The present invention is based on such findings.

The present invention provides [1] to [12] listed below.
[1] A marker peptide that is selected from the group consisting of following (A) to (J) and is for determining a risk of developing metabolic syndrome:
(A) a polypeptide comprising ten or more consecutive amino acid residues in the amino acid sequence of SEQ ID NO:1;
(B) a polypeptide comprising an amino acid sequence having one or several amino acid deletions, additions, substitutions or insertions in ten or more consecutive amino acid residues in the amino acid sequence of SEQ ID NO:1 and capable of being used as a marker for determining the risk of developing the metabolic syndrome;
(C) a polypeptide comprising an amino acid sequence having 90% or more homology to ten or more consecutive amino acid residues in the amino acid sequence of SEQ ID NO:1 and capable of being used as the marker for determining the risk of developing the metabolic syndrome;
(D) a polypeptide comprising ten or more consecutive amino acid residues in an amino acid sequence having one or several amino acid deletions, additions, substitutions or insertions in the amino acid sequence of SEQ ID NO:1 and capable of being used as the marker for determining the risk of developing the metabolic syndrome;
(E) a polypeptide comprising ten or more consecutive amino acid residues in an amino acid sequence having 90% or more homology to the amino acid sequence of SEQ ID NO:1 and capable of being used as the marker for determining the risk of developing the metabolic syndrome;
(F) a polypeptide comprising ten or more consecutive amino acid residues in the amino acid sequence of SEQ ID NO:2;
(G) a polypeptide comprising an amino acid sequence having one or several amino acid deletions, additions, substitutions or insertions in ten or more consecutive amino acid residues in the amino acid sequence of SEQ ID NO:2 and capable of being used as the marker for determining the risk of developing the metabolic syndrome;
(H) a polypeptide comprising an amino acid sequence having 90% or more homology to ten or more consecutive amino acid residues in the amino acid sequence of SEQ ID NO:2;
(I) a polypeptide comprising ten or more consecutive amino acid residues in an amino acid sequence having one or several amino acid deletions, additions, substitutions or insertions in the amino acid sequence of SEQ ID NO:2 and capable of being used as the marker for determining the risk of developing the metabolic syndrome; and
(J) a polypeptide comprising ten or more consecutive amino acid residues in an amino acid sequence having 90% or more homology to the amino acid sequence of SEQ ID NO:2 and capable of being used as the marker for determining the risk of developing the metabolic syndrome.
[2] An antibody or an aptamer bound to the marker peptide for determining the risk of developing the metabolic syndrome according to [1].
[3] A microarray in which an antibody or an aptamer bound to the marker peptide for determining the risk of developing the metabolic syndrome according to [1] has been immobilized to a carrier.
[4] A method for determining a risk of developing metabolic syndrome, comprising measuring an amount or the presence or absence of the marker peptide for determining the risk of developing the metabolic syndrome according to [1] in a biological sample collected from a subject.

[5] The method according to [4], wherein the risk of developing the metabolic syndrome is determined to be high when an amount of the marker peptide for determining the risk of developing the metabolic syndrome according to [1] in the biological sample collected from the subject is higher than an amount in a biological sample collected from a healthy person.

[6] The method according to [4], wherein the risk of developing the metabolic syndrome is determined to be high when an amount of the marker peptide for determining the risk of developing the metabolic syndrome according to [1] in the biological sample collected from the subject is equivalent to or higher than an amount in a biological sample collected from a patient with metabolic syndrome.

[7] The method according to any one of [4] to [6], wherein the amount of the marker peptide for determining the risk of developing the metabolic syndrome according to [1] is measured by a method selected from a mass spectrometry, an immunoassay using the antibody or the aptamer according to [2] and an immunoassay using the microarray according to [3].

[8] The method according to [4], wherein multivariate analysis is performed using a combination of two or more marker peptides for determining the risk of developing the metabolic syndrome as variables.

[9] The method according to [8], wherein the multivariate analysis is a logistic regression analysis.

[10] The method according to any one of [4] to [9], wherein the biological sample is a saliva sample.

[11] A kit for determining a risk of developing metabolic syndrome, comprising the antibody or the aptamer according to [2], or the microarray according to [3].

[12] The kit according to [11] further comprising a gum.

The present invention is applicable to diagnosis of the metabolic syndrome. Examples of methods for the diagnosis of the metabolic syndrome may include the following aspects.

[13] A marker peptide that is selected from the group consisting of the above (A) to (J) and is for diagnosis of metabolic syndrome.

[14] An antibody or an aptamer bound to the marker peptide for the diagnosis of the metabolic syndrome according to [13].

[15] A microarray in which an antibody or an aptamer bound to the marker peptide for the diagnosis of the metabolic syndrome according to [13].

[16] A method for diagnosis of metabolic syndrome, comprising measuring an amount or the presence or absence of the marker peptide for the diagnosis of the metabolic syndrome according to [13] in a biological sample collected from a subject.

[17] The method for the diagnosis according to [16], wherein the subject is a human.

[18] The method for the diagnosis according to [16] or [17], wherein the subject is determined to develop the metabolic syndrome when an amount of the marker peptide for the diagnosis of the metabolic syndrome according to [13] in a biological sample collected from the subject is higher than an amount in a biological sample collected from a healthy person.

[19] The method for the diagnosis according to [16] or [17], wherein the subject is determined to develop the metabolic syndrome when an amount of the marker peptide for the diagnosis of the metabolic syndrome according to [13] in a biological sample collected from the subject is equivalent to or higher than an amount in a biological sample collected from a patient with metabolic syndrome.

[20] The method for the diagnosis according to any one of [16] to [19], wherein the amount of the marker peptide for the diagnosis of the metabolic syndrome according to [13] is measured by a method selected from a mass spectrometry, an immunoassay using the antibody or the aptamer according to [14] and an immunoassay using the microarray according to [15].

[21] The method for the diagnosis according to [16] or [17], wherein multivariate analysis is performed using a combination of two or more marker peptides for the diagnosis of the metabolic syndrome as variables.

[22] The method for the diagnosis according to [21], wherein the multivariate analysis is a logistic regression analysis.

[23] The method for the diagnosis according to any one of [16] to [22], wherein the biological sample is a saliva sample.

[24] A kit for diagnosis of metabolic syndrome, comprising the antibody or the aptamer according to [14], or the microarray according to [15].

[25] The kit according to [24] further comprising a gum.

Effect of the Invention

According to the present invention, the risk of developing the metabolic syndrome can be determined with good accuracy. When the risk of developing the metabolic syndrome is determined using the present invention prior to diagnosis by a physician, the metabolic syndrome can be prevented early and development of the metabolic syndrome can be obviated.

DESCRIPTION OF EMBODIMENTS

Figure 1:
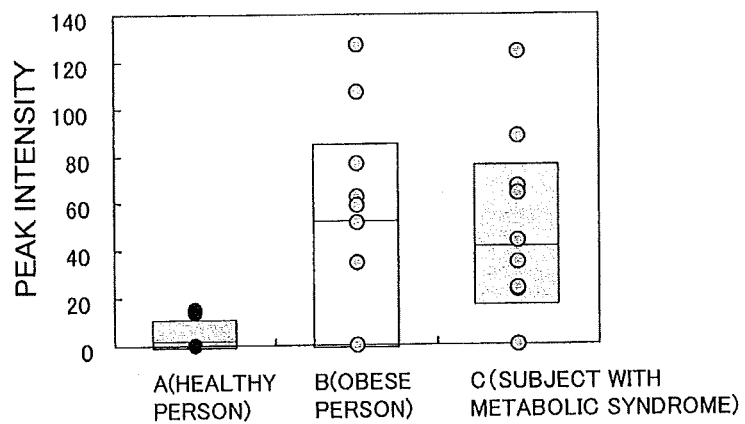
FIG. 1 is a graph showing a peak intensity of a P-B peptide fragment $(1)^{27-54}$ in each subject group.

The present invention relates to determination of a risk of developing metabolic syndrome. The determination of the risk of developing the metabolic syndrome in the present invention means determining (evaluating, discriminating, differentiating, estimating) whether a subject has developed the metabolic syndrome or not, has been already cured or not, or will be potentially develop it in future, or distinguishing (classifying) whether the subject has the risk of developing the metabolic syndrome or not. The determination of the risk of development means determining whether a subject has developed the metabolic syndrome or not, has been already cured or not, or will potentially develop it in future or not. An accuracy in the determination of the risk of developing the metabolic syndrome is generally an extent that the risk of developing the metabolic syndrome can correctly be determined in subjects in statistically significant percentage in subjects, and is an extent that the risk of developing the metabolic syndrome can correctly be determined in 50% or more, 60% or more, 70% or more, 80% or more, 85% or more, or 90% or more subjects. The determination method of the present invention is useful as a preliminary determination method prior to the diagnosis by the physician.

The metabolic syndrome in the present invention refers to a condition in which hyperglycemia, hypertension or hyperlipidemia is caused due to visceral fat type obesity.

The metabolic syndrome means corresponding to any one or more of (a) to (d) shown in Example according to the standard defined for Japanese by Japan Society for the Study of Obesity (2005).

A subject in the present invention is generally an animal, preferably a human, an experimental animal such as mouse, rat, guinea pig, hamster, and rabbit, and more preferably a human.

(1) Marker Peptides of the Present Invention

The marker peptides for determining the risk of developing the metabolic syndrome in the present invention are one or more selected from the group consisting of (A) to (J) above.

When the risk of developing the metabolic syndrome is determined using the marker peptide for determining the risk of developing the metabolic syndrome in the present invention, one selected from (A) to (J) may be used, but the more highly accurate determination is possible by combining two or more thereof. When two or more peptides are combined, it is preferable to combine one or more peptides selected from the group consisting of (A) to (E) with one or more peptides selected from the group consisting of (F) to (J). Preferable examples of the combination of two or more peptides will be listed in (4) below.

(1-1) Concerning (A) to (C)

In (A) to (C), the amino acid sequence of SEQ ID NO:1 is an amino acid sequence encoding a human P-B peptide (submaxillary gland androgen-regulated protein 3B, Proline-rich peptide P-B, Proline-rich protein 3) (79 amino acids in full length). The P-B peptide is a peptide belonging to a proline-rich protein (PRP) family containing proline (P) abundantly.

In (A) to (C), ten or more consecutive amino acid residues in the amino acid sequence of SEQ ID NO:1 are preferably 11 or more consecutive amino acid residues, more preferably 12 or more consecutive amino acid residues, and still more preferably 13 or more consecutive amino acid residues in the amino acid sequence of SEQ ID NO:1. An upper limit is not particularly defined, and the length of the ten or more consecutive amino acid residues may be or may exceed the full length (79 residues) of the amino acid sequence of SEQ ID NO:1, but is, for example, 100 or less, 90 or less, 80 or less, 70 or less, and 60 or less.

In (A) to (C), ten or more amino acid residues preferably include at least a portion of amino acid residues at positions 27 to 54, at least a portion of amino acid residues at positions 23 to 54, at least a portion of amino acid residues at positions 55 to 79, at least a portion of amino acid residues at positions 23 to 79, or at least a portion of amino acid residues at positions 23 to 35 in the ten or more consecutive amino acid residues in the amino acid sequence of SEQ ID NO:1. It is more preferable that the ten or more amino acid residues include ten or more consecutive amino acid residues in the amino acid residues at positions 27 to 54, ten or more consecutive amino acid residues in the amino acid residues at positions 23 to 54, ten or more consecutive amino acid residues in the amino acid residues at positions 55 to 79, ten or more consecutive amino acid residues in the amino acid residues at positions 23 to 79, or ten or more consecutive amino acid residues in the amino acid residues at positions 23 to 35 in the amino acid sequence of SEQ ID NO:1. It is still more preferable that the ten or more amino acid residues correspond to an amino acid sequence at positions 27 to 54, an amino acid sequence at positions 23 to 54, an amino acid sequence at positions 55 to 79, an amino acid sequence at positions 23 to 79, or an amino acid sequence at positions 23 to 35 in the amino acid sequence of SEQ ID NO:1.

(A) may be a polypeptide comprising ten or more consecutive amino acid residues in the amino acid sequence of SEQ ID NO:1, and is preferably a polypeptide consisting of the ten or more consecutive amino acid residues in the amino acid sequence of SEQ ID NO:1.

(B) may be a polypeptide comprising an amino acid sequence having one or several amino acid deletions, additions, substitutions or insertions in ten or more consecutive amino acid residues in the amino acid sequence of SEQ ID NO:1 and capable of being used as the marker for determining the risk of developing the metabolic syndrome, and is preferably a polypeptide consisting of the amino acid sequence having one or several amino acid deletions, additions, substitutions or insertions in ten or more consecutive amino acid residues in the amino acid sequence of SEQ ID NO:1 and capable of being used as the marker for determining the risk of developing the metabolic syndrome.

(C) may be a polypeptide comprising an amino acid sequence having 90% or more homology to ten or more consecutive amino acid residues in the amino acid sequence of SEQ ID NO:1 and capable of being used as the marker for determining the risk of developing the metabolic syndrome, and is preferably a polypeptide consisting of an amino acid sequence having 90% or more homology to ten or more consecutive amino acid residues in the amino acid sequence of SEQ ID NO:1 and capable of being used as the marker for determining the risk of developing the metabolic syndrome.

In (B), the mutations of one or several amino acid residues may be present in one region but may be present in multiple different regions in the amino acid sequence. The term "one or several" refers to a range in which a function or a property of the marker peptide is not largely impaired. "One or several" refers to, for example, "one or three", "one or two", or "one."

A position at which the mutation (deletion, addition, substitution or insertion) of an amino acid residue is permitted is obvious to those skilled in the art. Specifically, those skilled in the art (1) can compare amino acid sequences of a plurality of proteins, having the same type activity (e.g., the amino acid sequence represented by SEQ ID NO:1, and amino acid sequences of the other marker peptides for determining the risk of developing the metabolic syndrome), (2) demonstrate relatively conserved regions and relatively not conserved regions, and (3) predict regions capable of playing a functionally important role and regions not capable of playing the functionally important role from the relatively conserved regions and the relatively not conserved regions, and thus can recognize correlativity between the structure and the function. Therefore, those skilled in the art can estimate the position of the amino acid residue, the mutation of which is permitted in the amino acid sequence of the marker for determining the risk of developing the metabolic syndrome.

When the mutation by substitution of an amino acid residue is included, the substitution of the amino acid residue may be conservative substitution. The term "conservative substitution" as used herein refers to substituting a predetermined amino acid residue with an amino acid residue having a similar side chain. Families of amino acid residues having the similar side chain are well-known in the art, and examples thereof may include amino acids having a basic side chain (e.g., lysine, arginine, histidine), amino acids having an acidic side chain (e.g., aspartic acid, glutamic acid), amino acids having a non-charged polar side chain (e.g., asparagine, glutamine, serine, threonine, tyrosine, cysteine), amino acids having a non-polar side chain (e.g., glycine, alanine, valine, leucine, isoleucine, proline, phenylalanine, methionine, tryptophan), amino acids having a side chain branched at position β (e.g., threonine, valine, isoleucine), amino acids having an aromatic side chain (e.g., tyrosine, phenylalanine, tryptophan, histidine), amino acids having a side chain containing a hydroxyl group (e.g., alcoholic, phenolic) (e.g., serine, threonine, tyrosine), and amino acids having a sulfur-containing side chain (e.g., cysteine, methionine). Preferably, the conservative substitution of the amino acid residues may be substitution between aspartic acid and glutamic acid, substitution between arginine and lysine and histidine, substitution between tryptophan and phenylalanine, substitution between phenylalanine and valine, substitution between leucine and isoleucine and alanine, and substitution between glycine and alanine.

In (C), the homology (e.g., identity, similarity) to the amino acid sequence is 90% or more, preferably 95%, more preferably 98% or more, and still more preferably 99% or more.

The homology (e.g., identity, similarity) to the amino acid sequence can be determined using algorithm by Karlin and Altschul, BLAST (Pro. Natl. Acad. Sci. USA, 90, 5873 (1993)) or FASTA by Pearson (Methods Enzymol., 183, 63 (1990)). Programs called BLASTP and BLASTN have been developed based on the algorithm BLAST, and thus, the homology of the amino acid sequences may be calculated using these programs with default setting.

Examples of (A) may include (A-1) to (A-33):

(A-1) a polypeptide consisting of ten or more consecutive amino acid residues in the amino acid sequence of SEQ ID NO:1;

(A-2) a polypeptide which comprises ten or more consecutive amino acid residues in the amino acid sequence of SEQ ID NO:1, and in which at least a portion of amino acid residues at positions 27 to 54 is included in the ten or more consecutive amino acid residues;

(A-3) a polypeptide which consists of ten or more consecutive amino acid residues in the amino acid sequence of SEQ ID NO:1, and in which at least a portion of the amino acid residues at position 27 to 54 is included in the ten or more consecutive amino acid residues;

(A-4) a polypeptide comprising ten or more consecutive amino acid residues selected from the amino acid residues at positions 27 to 54 in the amino acid sequence of SEQ ID NO:1;

(A-5) a polypeptide consisting of ten or more consecutive amino acid residues selected from the amino acid residues at positions 27 to 54 in the amino acid sequence of SEQ ID NO:1;

(A-6) a polypeptide comprising the amino acid residues at positions 27 to 54 in the amino acid sequence of SEQ ID NO:1;

(A-7) a polypeptide consisting of the amino acid residues at positions 27 to 54 in the amino acid sequence of SEQ ID NO:1;

(A-8) a polypeptide which comprises ten or more consecutive amino acid residues in the amino acid sequence of SEQ ID NO:1, and in which at least a portion of amino acid residues at positions 23 to 54 is included in the ten or more consecutive amino acid residues;

(A-9) a polypeptide which consists of ten or more consecutive amino acid residues in the amino acid sequence of SEQ ID NO:1, and in which at least a portion of the amino acid residues at positions 23 to 54 is included in the ten or more consecutive amino acid residues;

(A-10) a polypeptide comprising ten or more consecutive amino acid residues selected from the amino acid residues at positions 23 to 54 in the amino acid sequence of SEQ ID NO:1;

(A-11) a polypeptide consisting of ten or more consecutive amino acid residues selected from the amino acid residues at positions 23 to 54 in the amino acid sequence of SEQ ID NO:1;

(A-12) a polypeptide comprising the amino acid residues at positions 23 to 54 in the amino acid sequence of SEQ ID NO:1;

(A-13) a polypeptide consisting of the amino acid residues at positions 23 to 54 in the amino acid sequence of SEQ ID NO:1;

(A-14) a polypeptide which comprises ten or more consecutive amino acid residues in the amino acid sequence of SEQ ID NO:1, and in which at least a portion of amino acid residues at positions 55 to 79 is included in the ten or more consecutive amino acid residues;

(A-15) a polypeptide which consists of ten or more consecutive amino acid residues in the amino acid sequence of SEQ ID NO:1, and in which at least a portion of the amino acid residues at positions 55 to 79 is included in the ten or more consecutive amino acid residues;

(A-16) a polypeptide comprising ten or more consecutive amino acid residues selected from the amino acid residues at positions 55 to 79 in the amino acid sequence of SEQ ID NO:1;

(A-17) a polypeptide consisting of ten or more consecutive amino acid residues selected from the amino acid residues at positions 55 to 79 in the amino acid sequence of SEQ ID NO:1;

(A-18) a polypeptide comprising the amino acid residues at positions 55 to 79 in the amino acid sequence of SEQ ID NO:1;

(A-19) a polypeptide consisting of the amino acid residues at positions 55 to 79 in the amino acid sequence of SEQ ID NO:1;

(A-20) a polypeptide which comprises ten or more consecutive amino acid residues in the amino acid sequence of SEQ ID NO:1, and in which at least a portion of amino acid residues at positions 23 to 79 is included in the ten or more consecutive amino acid residues;

(A-21) a polypeptide which consists of ten or more consecutive amino acid residues in the amino acid sequence of SEQ ID NO:1, and in which at least a portion of the amino acid residues at positions 23 to 79 is included in the ten or more consecutive amino acid residues;

(A-22) a polypeptide comprising ten or more consecutive amino acid residues selected from the amino acid residues at positions 23 to 79 in the amino acid sequence of SEQ ID NO:1;

(A-23) a polypeptide consisting of ten or more consecutive amino acid residues selected from the amino acid residues at positions 23 to 79 in the amino acid sequence of SEQ ID NO:1;

(A-24) a polypeptide comprising the amino acid residues at positions 23 to 79 in the amino acid sequence of SEQ ID NO:1;

(A-25) a polypeptide consisting of the amino acid residues at positions 23 to 79 in the amino acid sequence of SEQ ID NO:1;

(A-26) a polypeptide which comprises ten or more consecutive amino acid residues in the amino acid sequence of SEQ ID NO:1, and in which at least a portion of amino acid residues at positions 23 to 35 is included in the ten or more consecutive amino acid residues;

(A-27) a polypeptide which consists of ten or more consecutive amino acid residues in the amino acid sequence of SEQ ID NO:1, and in which at least a portion of the amino acid residues at positions 23 to 35 is included in the ten or more consecutive amino acid residues;

(A-28) a polypeptide comprising ten or more consecutive amino acid residues selected from the amino acid residues at positions 23 to 35 in the amino acid sequence of SEQ ID NO:1;

(A-29) a polypeptide consisting of ten or more consecutive amino acid residues selected from the amino acid residues at positions 23 to 35 in the amino acid sequence of SEQ ID NO:1;

(A-30) a polypeptide comprising the amino acid residues at positions 23 to 35 in the amino acid sequence of SEQ ID NO:1;

(A-31) a polypeptide consisting of the amino acid residues at positions 23 to 35 in the amino acid sequence of SEQ ID NO:1;

(A-32) a polypeptide comprising the amino acid sequence of SEQ ID NO:1; and (A-33) a polypeptide consisting of the amino acid sequence of SEQ ID NO:1.

Examples of (B) may include (B-1) to (B-33):

(B-1) a polypeptide consisting of an amino acid sequence having one or several amino acid deletions, additions, substitutions and insertions in ten or more consecutive amino acid residues in the amino acid sequence of SEQ ID NO:1, and capable of being used as the marker for determining the risk of developing the metabolic syndrome;

(B-2) a polypeptide comprising an amino acid sequence having one or several amino acid deletions, additions, substitutions and insertions in an amino acid sequence that comprises ten or more consecutive amino acid residues in the amino acid sequence of SEQ ID NO:1 and includes at least a portion of amino acid residues at positions 27 to 54 in the ten or more consecutive amino acid residues, and can be used as the marker for determining the risk of developing the metabolic syndrome;

(B-3) a polypeptide consisting of an amino acid sequence having one or several amino acid deletions, additions, substitutions and insertions in an amino acid sequence that comprises ten or more consecutive amino acid residues in the amino acid sequence of SEQ ID NO:1 and includes at least a portion of the amino acid residues at positions 27 to 54 in the ten or more consecutive amino acid residues, and can be used as the marker for determining the risk of developing the metabolic syndrome;

(B-4) a polypeptide comprising an amino acid sequence having one or several amino acid deletions, additions, substitutions and insertions in ten or more consecutive amino acid residues selected from the amino acid residues at positions 27 to 54 in the amino acid sequence of SEQ ID NO:1, and capable of being used as the marker for determining the risk of developing the metabolic syndrome;

(B-5) a polypeptide consisting of an amino acid sequence having one or several amino acid deletions, additions, substitutions and insertions in ten or more consecutive amino acid residues selected from the amino acid residues at positions 27 to 54 in the amino acid sequence of SEQ ID NO:1, and capable of being used as the marker for determining the risk of developing the metabolic syndrome;

(B-6) a polypeptide comprising an amino acid sequence having one or several amino acid deletions, additions, substitutions and insertions in an amino acid sequence of the amino acid residues at positions 27 to 54 in the amino acid sequence of SEQ ID NO:1, and capable of being used as the marker for determining the risk of developing the metabolic syndrome;

(B-7) a polypeptide consisting of an amino acid sequence having one or several amino acid deletions, additions, substitutions and insertions in the amino acid sequence of the amino acid residues at positions 27 to 54 in the amino acid sequence of SEQ ID NO:1, and capable of being used as the marker for determining the risk of developing the metabolic syndrome;

(B-8) a polypeptide comprising an amino acid sequence having one or several amino acid deletions, additions, substitutions and insertions in an amino acid sequence that comprises ten or more consecutive amino acid residues in the amino acid sequence of SEQ ID NO:1 and includes at least a portion of amino acid residues at positions 23 to 54 in the ten or more consecutive amino acid residues, and can be used as the marker for determining the risk of developing the metabolic syndrome;

(B-9) a polypeptide consisting of an amino acid sequence having one or several amino acid deletions, additions, substitutions and insertions in an amino acid sequence that comprises ten or more consecutive amino acid residues in the amino acid sequence of SEQ ID NO:1 and includes at least a portion of the amino acid residues at positions 23 to 54 in the ten or more consecutive amino acid residues, and can be used as the marker for determining the risk of developing the metabolic syndrome;

(B-10) a polypeptide comprising an amino acid sequence having one or several amino acid deletions, additions, substitutions and insertions in ten or more consecutive amino acid residues selected from the amino acid residues at positions 23 to 54 in the amino acid sequence of SEQ ID NO:1, and capable of being used as the marker for determining the risk of developing the metabolic syndrome;

(B-11) a polypeptide consisting of an amino acid sequence having one or several amino acid deletions, additions, substitutions and insertions in ten or more consecutive amino acid residues selected from the amino acid residues at positions 23 to 54 in the amino acid sequence of SEQ ID NO:1, and capable of being used as the marker for determining the risk of developing the metabolic syndrome;

(B-12) a polypeptide comprising an amino acid sequence having one or several amino acid deletions, additions, substitutions and insertions in an amino acid sequence of the amino acid residues at positions 23 to 54 in the amino acid sequence of SEQ ID NO:1, and capable of being used as the marker for determining the risk of developing the metabolic syndrome;

(B-13) a polypeptide consisting of an amino acid sequence having one or several amino acid deletions, additions, substitutions and insertions in the amino acid sequence of the amino acid residues at positions 23 to 54 in the amino acid sequence of SEQ ID NO:1, and capable of being used as the marker for determining the risk of developing the metabolic syndrome;

(B-14) a polypeptide comprising an amino acid sequence having one or several amino acid deletions, additions, substitutions and insertions in an amino acid sequence that comprises ten or more consecutive amino acid residues in the amino acid sequence of SEQ ID NO:1 and includes at least a portion of amino acid residues at positions 55 to 79 in the ten or more consecutive amino acid residues, and can be used as the marker for determining the risk of developing the metabolic syndrome;

(B-15) a polypeptide consisting of an amino acid sequence having one or several amino acid deletions, additions, substitutions and insertions in an amino acid sequence that comprises ten or more consecutive amino acid residues in the amino acid sequence of SEQ ID NO:1 and includes at least a portion of the amino acid residues at positions 55 to 79 in the ten or more consecutive amino acid residues, and can be used as the marker for determining the risk of developing the metabolic syndrome;

(B-16) a polypeptide comprising an amino acid sequence having one or several amino acid deletions, additions, substitutions and insertions in ten or more consecutive amino acid residues selected from the amino acid residues at positions 55 to 79 in the amino acid sequence of SEQ ID NO:1, and capable of being used as the marker for determining the risk of developing the metabolic syndrome;

(B-17) a polypeptide consisting of an amino acid sequence having one or several amino acid deletions, additions, substitutions and insertions in ten or more consecutive amino acid residues selected from the amino acid residues at positions 55 to 79 in the amino acid sequence of SEQ ID NO:1, and capable of being used as the marker for determining the risk of developing the metabolic syndrome;

(B-18) a polypeptide comprising an amino acid sequence having one or several amino acid deletions, additions, substitutions and insertions in an amino acid sequence of the amino acid residues at positions 55 to 79 in the amino acid sequence of SEQ ID NO:1, and capable of being used as the marker for determining the risk of developing the metabolic syndrome;

(B-19) a polypeptide consisting of an amino acid sequence having one or several amino acid deletions, additions, substitutions and insertions in the amino acid sequence of the amino acid residues at positions 55 to 79 in the amino acid sequence of SEQ ID NO:1, and capable of being used as the marker for determining the risk of developing the metabolic syndrome;

(B-20) a polypeptide comprising an amino acid sequence having one or several amino acid deletions, additions, substitutions and insertions in an amino acid sequence that comprises ten or more consecutive amino acid residues in the amino acid sequence of SEQ ID NO:1 and includes at least a portion of amino acid residues at positions 23 to 79 in the ten or more consecutive amino acid residues, and can be used as the marker for determining the risk of developing the metabolic syndrome;

(B-21) a polypeptide consisting of an amino acid sequence having one or several amino acid deletions, additions, substitutions and insertions in an amino acid sequence that comprises ten or more consecutive amino acid residues in the amino acid sequence of SEQ ID NO:1 and includes at least a portion of the amino acid residues at positions 23 to 79 in the ten or more consecutive amino acid residues, and can be used as the marker for determining the risk of developing the metabolic syndrome;

(B-22) a polypeptide comprising an amino acid sequence having one or several amino acid deletions, additions, substitutions and insertions in ten or more consecutive amino acid residues selected from the amino acid residues at positions 23 to 79 in the amino acid sequence of SEQ ID NO:1, and capable of being used as the marker for determining the risk of developing the metabolic syndrome;

(B-23) a polypeptide consisting of an amino acid sequence having one or several amino acid deletions, substitutions and insertions in ten or more consecutive amino acid residues selected from the amino acid residues at positions 23 to 79 in the amino acid sequence of SEQ ID NO:1, and capable of being used as the marker for determining the risk of developing the metabolic syndrome;

(B-24) a polypeptide comprising an amino acid sequence having one or several amino acid deletions, additions, substitutions and insertions in an amino acid sequence of the amino acid residues at positions 23 to 79 in the amino acid sequence of SEQ ID NO:1, and capable of being used as the marker for determining the risk of developing the metabolic syndrome;

(B-25) a polypeptide consisting of an amino acid sequence having one or several amino acid deletions, additions, substitutions and insertions in the amino acid sequence of the amino acid residues at positions 23 to 79 in the amino acid sequence of SEQ ID NO:1, and capable of being used as the marker for determining the risk of developing the metabolic syndrome;

(B-26) a polypeptide comprising an amino acid sequence having one or several amino acid deletions, additions, substitutions and insertions in an amino acid sequence that comprises ten or more consecutive amino acid residues in the amino acid sequence of SEQ ID NO:1 and includes at least a portion of amino acid residues at positions 23 to 35 in the ten or more consecutive amino acid residues, and can be used as the marker for determining the risk of developing the metabolic syndrome;

(B-27) a polypeptide consisting of an amino acid sequence having one or several amino acid deletions, additions, substitutions and insertions in an amino acid sequence that comprises ten or more consecutive amino acid residues in the amino acid sequence of SEQ ID NO:1 and includes at least a portion of the amino acid residues at positions 23 to 35 in the ten or more consecutive amino acid residues, and can be used as the marker for determining the risk of developing the metabolic syndrome;

(B-28) a polypeptide comprising an amino acid sequence having one or several amino acid deletions, additions, substitutions and insertions in ten or more consecutive amino acid residues selected from the amino acid residues at positions 23 to 35 in the amino acid sequence of SEQ ID NO:1, and capable of being used as the marker for determining the risk of developing the metabolic syndrome;

(B-29) a polypeptide consisting of an amino acid sequence having one or several amino acid deletions, additions, substitutions and insertions in ten or more consecutive amino acid residues selected from the amino acid residues at positions 23 to 35 in the amino acid sequence of SEQ ID NO:1, and capable of being used as the marker for determining the risk of developing the metabolic syndrome;

(B-30) a polypeptide comprising an amino acid sequence having one or several amino acid deletions, additions, substitutions and insertions in an amino acid sequence of the amino acid residues at positions 23 to 35 in the amino acid sequence of SEQ ID NO:1, and capable of being used as the marker for determining the risk of developing the metabolic syndrome;

(B-31) a polypeptide consisting of an amino acid sequence having one or several amino acid deletions, additions, substitutions and insertions in the amino acid sequence of the amino acid residues at positions 23 to 35 in the amino acid sequence of SEQ ID NO:1, and capable of being used as the marker for determining the risk of developing the metabolic syndrome;

(B-32) a polypeptide comprising an amino acid sequence having one or more amino acid deletions, additions, substitutions and insertions in the amino acid sequence of SEQ ID NO:1, and capable of being used as the marker for determining the risk of developing the metabolic syndrome; and (B-33) a polypeptide consisting of an amino acid sequence having one or more amino acid deletions, additions, substitutions and insertions in the amino acid sequence of SEQ ID NO:1, and capable of being used as the marker for determining the risk of developing the metabolic syndrome.

Examples of (C) may include (C-1) to (C-33):

(C-1) a polypeptide consisting of an amino acid sequence having 90% or more homology to ten or more consecutive amino acid residues in the amino acid sequence of SEQ ID NO:1, and capable of being used as the marker for determining the risk of developing the metabolic syndrome;

(C-2) a polypeptide comprising an amino acid sequence having 90% or more homology to an amino acid sequence that comprises ten or more consecutive amino acid residues in the amino acid sequence of SEQ ID NO:1 and includes at least a portion of amino acid residues at positions 27 to 54 in the ten or more consecutive amino acid residues, and can be used as the marker for determining the risk of developing the metabolic syndrome;

(C-3) a polypeptide consisting of an amino acid sequence having 90% or more homology to an amino acid sequence that comprises ten or more consecutive amino acid residues in the amino acid sequence of SEQ ID NO:1 and includes at least a portion of the amino acid residues at positions 27 to 54 in the ten or more consecutive amino acid residues, and can be used as the marker for determining the risk of developing the metabolic syndrome;

(C-4) a polypeptide comprising an amino acid sequence having 90% or more homology to ten or more consecutive amino acid residues selected from the amino acid residues at positions 27 to 54 in the amino acid sequence of SEQ ID NO:1, and capable of being used as the marker for determining the risk of developing the metabolic syndrome;

(C-5) a polypeptide consisting of an amino acid sequence having 90% or more homology to ten or more consecutive amino acid residues selected from the amino acid residues at positions 27 to 54 in the amino acid sequence of SEQ ID NO:1, and capable of being used as the marker for determining the risk of developing the metabolic syndrome;

(C-6) a polypeptide comprising an amino acid sequence having 90% or more homology to an amino acid sequence of the amino acid residues at positions 27 to 54 in the amino acid sequence of SEQ ID NO:1, and capable of being used as the marker for determining the risk of developing the metabolic syndrome;

(C-7) a polypeptide consisting of an amino acid sequence having 90% or more homology to the amino acid sequence of the amino acid residues at positions 27 to 54 in the amino acid sequence of SEQ ID NO:1, and capable of being used as the marker for determining the risk of developing the metabolic syndrome;

(C-8) a polypeptide comprising an amino acid sequence having 90% or more homology to an amino acid sequence that comprises ten or more consecutive amino acid residues in the amino acid sequence of SEQ ID NO:1 and includes at least a portion of the amino acid residues at positions 23 to 54 in the ten or more consecutive amino acid residues, and can be used as the marker for determining the risk of developing the metabolic syndrome;

(C-9) a polypeptide consisting of an amino acid sequence having 90% or more homology to an amino acid sequence that comprises ten or more consecutive amino acid residues in the amino acid sequence of SEQ ID NO:1 and includes at least a portion of the amino acid residues at positions 23 to 54 in the ten or more consecutive amino acid residues, and can be used as the marker for determining the risk of developing the metabolic syndrome;

(C-10) a polypeptide comprising an amino acid sequence having 90% or more homology to ten or more consecutive amino acid residues selected from the amino acid residues at positions 23 to 54 in the amino acid sequence of SEQ ID NO:1, and capable of being used as the marker for determining the risk of developing the metabolic syndrome;

(C-11) a polypeptide consisting of an amino acid sequence having 90% or more homology to ten or more consecutive amino acid residues selected from the amino acid residues at positions 23 to 54 in the amino acid sequence of SEQ ID NO:1, and capable of being used as the marker for determining the risk of developing the metabolic syndrome;

(C-12) a polypeptide comprising an amino acid sequence having 90% or more homology to an amino acid sequence of the amino acid residues at positions 23 to 54 in the amino acid sequence of SEQ ID NO:1, and capable of being used as the marker for determining the risk of developing the metabolic syndrome;

(C-13) a polypeptide consisting of an amino acid sequence having 90% or more homology to the amino acid sequence of the amino acid residues at positions 23 to 54 in the amino acid sequence of SEQ ID NO:1, and capable of being used as the marker for determining the risk of developing the metabolic syndrome;

(C-14) a polypeptide comprising an amino acid sequence having 90% or more homology to an amino acid sequence that comprises ten or more consecutive amino acid residues in the amino acid sequence of SEQ ID N0:1 and includes at least a portion of amino acid residues at positions 55 to 79 in the ten or more consecutive amino acid residues, and can be used as the marker for determining the risk of developing the metabolic syndrome;

(C-15) a polypeptide consisting of an amino acid sequence having 90% or more homology to an amino acid sequence that comprises ten or more consecutive amino acid residues in the amino acid sequence of SEQ ID NO:1 and includes at least a portion of the amino acid residues at positions 55 to 79 in the ten or more consecutive amino acid residues, and can be used as the marker for determining the risk of developing the metabolic syndrome;

(C-16) a polypeptide comprising an amino acid sequence having 90% or more homology to ten or more consecutive amino acid residues selected from the amino acid residues at positions 55 to 79 in the amino acid sequence of SEQ ID NO:1, and capable of being used as the marker for determining the risk of developing the metabolic syndrome;

(C-17) a polypeptide consisting of an amino acid sequence having 90% or more homology to ten or more consecutive amino acid residues selected from the amino acid residues at positions 55 to 79 in the amino acid sequence of SEQ ID NO:1, and capable of being used as the marker for determining the risk of developing the metabolic syndrome;

(C-18) a polypeptide comprising an amino acid sequence having 90% or more homology to an amino acid sequence of the amino acid residues at positions 55 to 79 in the amino acid sequence of SEQ ID NO:1, and capable of being used as the marker for determining the risk of developing the metabolic syndrome;

(C-19) a polypeptide consisting of an amino acid sequence having 90% or more homology to the amino acid sequence of the amino acid residues at positions 55 to 79 in the amino acid sequence of SEQ ID NO:1, and capable of being used as the marker for determining the risk of developing the metabolic syndrome;

(C-20) a polypeptide comprising an amino acid sequence having 90% or more homology to an amino acid sequence that comprises ten or more consecutive amino acid residues in the amino acid sequence of SEQ ID NO:1 and includes at least a portion of amino acid residues at positions 23 to 79 in the ten or more consecutive amino acid residues, and can be used as the marker for determining the risk of developing the metabolic syndrome;

(C-21) a polypeptide consisting of an amino acid sequence having 90% or more homology to an amino acid sequence that comprises the ten or more consecutive amino acid residues in the amino acid sequence of SEQ ID NO:1 and includes at least a portion of the amino acid residues at positions 23 to 79 in the ten or more consecutive amino acid residues, and can be used as the marker for determining the risk of developing the metabolic syndrome;

(C-22) a polypeptide comprising an amino acid sequence having 90% or more homology to ten or more consecutive amino acid residues selected from the amino acid residues at positions 23 to 79 in the amino acid sequence of SEQ ID NO:1, and capable of being used as the marker for determining the risk of developing the metabolic syndrome;

(C-23) a polypeptide consisting of an amino acid sequence having 90% or more homology to ten or more consecutive amino acid residues selected from the amino acid residues at positions 23 to 79 in the amino acid sequence of SEQ ID NO:1, and capable of being used as the marker for determining the risk of developing the metabolic syndrome;

(C-24) a polypeptide comprising an amino acid sequence having 90% or more homology to an amino acid sequence of the amino acid residues at positions 23 to 79 in the amino acid sequence of SEQ ID N0:1, and capable of being used as the marker for determining the risk of developing the metabolic syndrome;

(C-25) a polypeptide consisting of an amino acid sequence having 90% or more homology to the amino acid sequence of the amino acid residues at positions 23 to 79 in the amino acid sequence of SEQ ID NO:1, and capable of being used as the marker for determining the risk of developing the metabolic syndrome;

(C-26) a polypeptide comprising an amino acid sequence having 90% or more homology to an amino acid sequence that comprises the ten or more consecutive amino acid residues in the amino acid sequence of SEQ ID NO:1 and includes at least a portion of amino acid residues at positions 23 to 35 in the ten or more consecutive amino acid residues, and can be used as the marker for determining the risk of developing the metabolic syndrome;

(C-27) a polypeptide consisting of an amino acid sequence having 90% or more homology to an amino acid sequence that comprises the ten or more consecutive amino acid residues in the amino acid sequence of SEQ ID NO:1 and includes at least a portion of the amino acid residues at positions 23 to 35 in the ten or more consecutive amino acid residues, and can be used as the marker for determining the risk of developing the metabolic syndrome;

(C-28) a polypeptide comprising an amino acid sequence having 90% or more homology to ten or more consecutive amino acid residues selected from the amino acid residues at positions 23 to 35 in the amino acid sequence of SEQ ID NO:1, and capable of being used as the marker for determining the risk of developing the metabolic syndrome;

(C-29) a polypeptide consists of an amino acid sequence having 90% or more homology to ten or more consecutive amino acid residues selected from the amino acid residues at positions 23 to 35 in the amino acid sequence of SEQ ID NO:1, and capable of being used as the marker for determining the risk of developing the metabolic syndrome;

(C-30) a polypeptide comprising an amino acid sequence having 90% or more homology to an amino acid sequence of the amino acid residues at positions 23 to 35 in the amino acid sequence of SEQ ID NO:1, and capable of being used as the marker for determining the risk of developing the metabolic syndrome;

(C-31) a polypeptide consisting of an amino acid sequence having 90% or more homology to the amino acid sequence of the amino acid residues at positions 23 to 35 in the amino acid sequence of SEQ ID NO:1, and capable of being used as the marker for determining the risk of developing the metabolic syndrome;

(C-32) a polypeptide comprising an amino acid sequence having 90% or more homology to the amino acid sequence of SEQ ID NO:1, and capable of being used as the marker for determining the risk of developing the metabolic syndrome; and (C-33) a polypeptide consisting of an amino acid sequence having 90% or more homology to the amino acid sequence of SEQ ID NO:1, and capable of being used as the marker for determining the risk of developing the metabolic syndrome.

(1-2) Concerning (D) and (E)

In (D) and (E), the description for the amino acid sequence of SEQ ID NO:1 is as described in (1-1) above.

In (D) and (E), ten or more consecutive amino acid residues in the amino acid sequence having each mutation in the amino acid sequence of SEQ ID NO:1 are preferably 11 or more consecutive amino acid residues, more preferably 12 or more consecutive amino acid residues, and still more preferably 13 or more consecutive amino acid residues. An upper limit is not particularly defined, and the length of the ten or more consecutive amino acid residue may be or may exceed a full length (79 residues) of the amino acid sequence having each mutation in the amino acid sequence of SEQ ID NO:1, but is, for example, 100 or less, 90 or less, 80 or less, 70 or less and 60 or less amino acid residues.

(D) may be a polypeptide comprising ten or more consecutive amino acid residues in an amino acid sequence having one or several amino acid deletions, additions, substitutions or insertions in the amino acid sequence of SEQ ID NO:1 and capable of being used as the marker for determining the risk of developing the metabolic syndrome, and is preferably a polypeptide consisting of ten or more consecutive amino acid residues in an amino acid sequence having one or several amino acid deletions, additions, substitutions or insertions in the amino acid sequence of SEQ ID NO:1 and capable of being used as the marker for determining the risk of developing the metabolic syndrome.

(E) may be a polypeptide comprising ten or more consecutive amino acid residues in an amino acid sequence having 90% or more homology to the amino acid sequence of SEQ ID NO:1 and capable of being used as the marker for determining the risk of developing the metabolic syndrome, and is preferably a polypeptide consisting of ten or more consecutive amino acid residues in an amino acid sequence having 90% or more homology to the amino acid sequence of SEQ ID NO:1 and capable of being used as the marker for determining the risk of developing the metabolic syndrome.

One or several amino acid mutations in (D) is the same as those described for (B) in (1-1) above.

The homology in (E) is the same as that described for (C) in (1-1) above.

A peptide selected from the group consisting of (A) to (E) is preferably a peptide selected from the group consisting of (A-2) to (A-31), (B-2) to (B-31) and (C-2) to (C-31), more preferably a peptide selected from the group consisting of (A-6), (A-7), (A-12), (A-13), (A-18), (A-19), (A-24), (A-25), (A-30) and (A-31), and still more preferably a peptide selected from the group consisting of (A-7), (A-13), (A-19), (A-25) and (A-31).

(1-3) Concerning (F) to (H)

In (F) to (H), the amino acid sequence of SEQ ID NO:2 is an amino acid sequence encoding human GIPR (gastric inhibitory polypeptide receptor, glucose-dependent insulinotropic polypeptide receptor) (466 amino acids in full length).

In (F) to (H), ten or more consecutive amino acid residues in the amino acid sequence of SEQ ID NO:2 are preferably 11 or more consecutive amino acid residues and more preferably 12 or more consecutive amino acid residues in the amino acid sequence of SEQ ID NO:2. An upper limit is not particularly defined, and the length of the ten or more consecutive amino acid residues may be or may exceed the full length (466 residues) of the amino acid sequence of SEQ ID NO:2, but is, for example, 500 or less, 400 or less, 300 or less, 200 or less, 100 or less, 90 or less, 80 or less, 70 or less, 60 or less, 50 or less, 40 or less, 30 or less, 25 or less, 20 or less, or 15 or less.

In (F) to (H), it is preferable that at least a portion of amino acid residues at positions 264 to 275 is included in the ten or more consecutive amino acid residues in the amino acid sequence of SEQ ID NO:2, and it is more preferable that the ten or more consecutive amino acid residues are ten or more consecutive amino acid residues in the amino acid residues at positions 264 to 275 in the amino acid sequence of SEQ ID NO:2. It is still more preferable that the ten or more consecutive amino acid residues correspond to an amino acid sequence of the amino acid residues at positions 264 to 275 or the amino acid sequence of SEQ ID NO:2.

(F) may be a polypeptide comprising ten or more consecutive amino acid residues in the amino acid sequence of SEQ ID NO:2, and is preferably a polypeptide consisting of the ten or more consecutive amino acid residues in the amino acid sequence of SEQ ID NO:2.

(G) may be a polypeptide comprising an amino acid sequence having one or several amino acid deletions, additions, substitutions or insertions in ten or more consecutive amino acid residues in the amino acid sequence of SEQ ID NO:2 and capable of being used as the marker for determining the risk of developing the metabolic syndrome, and is preferably a polypeptide consisting of an amino acid sequence having one or several amino acid deletions, additions, substitutions or insertions in ten or more consecutive amino acid residues in the amino acid sequence of SEQ ID NO:2 and capable of being used as the marker for determining the risk of developing the metabolic syndrome.

(H) may be a polypeptide comprising an amino acid sequence having 90% or more homology to ten or more consecutive amino acid residues in the amino acid sequence of SEQ ID NO:2 and capable of being used as the marker for determining the risk of developing the metabolic syndrome, and is preferably a polypeptide consisting of an amino acid sequence having 90% or more homology to ten or more consecutive amino acid residues in the amino acid sequence of SEQ ID NO:1 SEQ ID NO:2 and capable of being used as the marker for determining the risk of developing the metabolic syndrome.

One or several mutations in (G) is the same as those described for (B) in (1-1) above.

The homology in (H) is the same as that described for (C) in (1-1) above.

Examples of (F) may include (F-1) to (F-9):

(F-1) a polypeptide consisting of ten or more consecutive amino acid residues in the amino acid sequence of SEQ ID NO:2;

(F-2) a polypeptide which comprises ten or more consecutive amino acid residues in the amino acid sequence of SEQ ID NO:2, and in which at least a portion of amino acid residues at positions 264 to 275 is included in the ten or more consecutive amino acid residues;

(F-3) a polypeptide which consists of ten or more consecutive amino acid residues in the amino acid sequence of SEQ ID NO:2, and in which at least a portion of the amino acid residues at positions 264 to 275 is included in the ten or more consecutive amino acid residues;

(F-4) a polypeptide comprising ten or more consecutive amino acid residues selected from the amino acid residues at positions 264 to 275 in the amino acid sequence of SEQ ID NO:2;

(F-5) a polypeptide consisting of ten or more consecutive amino acid residues selected from the amino acid residues at positions 264 to 275 in the amino acid sequence of SEQ ID NO:2;

(F-6) a polypeptide comprising the amino acid residues at positions 264 to 275 in the amino acid sequence of SEQ ID NO:2;

(F-7) a polypeptide consisting of the amino acid residues at positions 264 to 275 in the amino acid sequence of SEQ ID NO:2;

(F-8) a polypeptide comprising the amino acid sequence of SEQ ID NO:2; and (F-9) a polypeptide consisting of the amino acid sequence of SEQ ID NO:2

Examples of (G) may include (G-1) and (G-9):

(G-1) a polypeptide consisting of an amino acid sequence having one or several amino acid deletions, additions, substitutions or insertions in ten or more consecutive amino acid residues in the amino acid sequence of SEQ ID NO:2 and capable of being used as the marker for determining the risk of developing the metabolic syndrome;

(G-2) a polypeptide comprising an amino acid sequence having one or several amino acid deletions, additions, substitutions or insertions in an amino acid sequence that comprises ten or more consecutive amino acid residues in the amino acid sequence of SEQ ID NO:2 and includes at least a portion of amino acid residues at positions 264 to 275 in the ten or more consecutive amino acid residues, and can be used as the marker for determining the risk of developing the metabolic syndrome;

(G-3) a polypeptide consisting of an amino acid sequence having one or several amino acid deletions, additions, substitutions or insertions in an amino acid sequence that comprises ten or more consecutive amino acid residues in the amino acid sequence of SEQ ID NO:2 and includes at least a portion of the amino acid residues at positions 264 to 275 in the ten or more consecutive amino acid residues, and can be used as the marker for determining the risk of developing the metabolic syndrome;

(G-4) a polypeptide comprising an amino acid sequence having one or several amino acid deletions, additions, substitutions or insertions in ten or more consecutive amino acid residues selected from the amino acid residues at positions 264 to 275 in the amino acid sequence of SEQ ID NO:2, and capable of being used as the marker for determining the risk of developing the metabolic syndrome;

(G-5) a polypeptide consisting of an amino acid sequence having one or several amino acid deletions, additions, substitutions or insertions in ten or more consecutive amino acid residues selected from the amino acid residues at positions 264 to 275 in the amino acid sequence of SEQ ID NO:2, and capable of being used as the marker for determining the risk of developing the metabolic syndrome;

(G-6) a polypeptide comprising an amino acid sequence having one or several amino acid deletions, additions, substitutions or insertions in an amino sequence of the amino acid residues at positions 264 to 275 in the amino acid sequence of SEQ ID NO:2, and capable of being used as the marker for determining the risk of developing the metabolic syndrome;

(G-7) a polypeptide consisting of an amino acid sequence having one or several amino acid deletions, additions, substitutions or insertions in an amino sequence of the amino acid residues at positions 264 to 275 in the amino acid sequence of SEQ ID NO:2, and capable of being used as the marker for determining the risk of developing the metabolic syndrome;

(G-8) a polypeptide comprising an amino acid sequence having one or several amino acid deletions, additions, substitutions or insertions in the amino acid sequence of SEQ ID NO:2, and capable of being used as the marker for determining the risk of developing the metabolic syndrome; and (G-9) a polypeptide consisting of an amino acid sequence having one or several amino acid deletions, additions, substitutions or insertions in the amino acid sequence of SEQ ID NO:2, and capable of being used as the marker for determining the risk of developing the metabolic syndrome.

Examples of (H) may include (H-1) to (H-9):

(H-1) a polypeptide consisting of an amino acid sequence having 90% or more homology to ten or more consecutive amino acid residues in the amino acid sequence of SEQ ID NO:2, and capable of being used as the marker for determining the risk of developing the metabolic syndrome;

(H-2) a polypeptide comprising an amino acid sequence having 90% or more homology to an amino acid sequence that comprises ten or more consecutive amino acid residues in the amino acid sequence of SEQ ID NO:2 and includes at least a portion of amino acid residues at positions 264 to 275 in the ten or more consecutive amino acid residues, and can be used as the marker for determining the risk of developing the metabolic syndrome;

(H-3) a polypeptide consisting of an amino acid sequence having 90% or more homology to an amino acid sequence that comprises ten or more consecutive amino acid residues in the amino acid sequence of SEQ ID NO:2 and includes at least a portion of the amino acid residues at positions 264 to 275 in the ten or more consecutive amino acid residues, and can be used as the marker for determining the risk of developing the metabolic syndrome;

(H-4) a polypeptide comprising an amino acid sequence having 90% or more homology to ten or more consecutive amino acid residues selected from the amino acid residues at positions 264 to 275 in the amino acid sequence of SEQ ID NO:2, and capable of being used as the marker for determining the risk of developing the metabolic syndrome;

(H-5) a polypeptide consisting of an amino acid sequence having 90% or more homology to ten or more consecutive amino acid residues selected from the amino acid residues at positions 264 to 275 in the amino acid sequence of SEQ ID NO:2, and capable of being used as the marker for determining the risk of developing the metabolic syndrome;

(H-6) a polypeptide comprising an amino acid sequence having 90% or more homology to an amino acid sequence of the amino acid residues at positions 264 to 275 in the amino acid sequence of SEQ ID NO:2, and capable of being used as the marker for determining the risk of developing the metabolic syndrome;

(H-7) a polypeptide consisting of an amino acid sequence having 90% or more homology to an amino acid sequence of the amino acid residues at positions 264 to 275 in the amino acid sequence of SEQ ID NO:2, and capable of being used as the marker for determining the risk of developing the metabolic syndrome;

(H-8) a polypeptide comprising an amino acid sequence having 90% or more homology to the amino acid sequence of SEQ ID NO:2, and capable of being used as the marker for determining the risk of developing the metabolic syndrome; and (H-9) a polypeptide consisting of an amino acid sequence having 90% or more homology to the amino acid sequence of SEQ ID NO:2, and capable of being used as the marker for determining the risk of developing the metabolic syndrome.

(1-4) Concerning (I) and (J)

The description for the amino acid sequence of SEQ ID NO:2 is the same as the description described in (1-3) above.

In (I) and (J), ten or more consecutive amino acid residues in an amino acid sequence having each mutation in the amino acid sequence of SEQ ID NO:2 is preferably 11 or more consecutive amino acid residues, and more preferably 12 or more consecutive amino acid residues. An upper limit is not particularly defined, and the length of the ten or more consecutive amino acid residues may be or may exceed the full length (466 residues) of the amino acid sequence of SEQ ID NO:2, but is, for example, 500 or less, 400 or less, 300 or less, 200 or less, 100 or less, 90 or less, 80 or less, 70 or less, 60 or less, 50 or less, 40 or less, 30 or less, 25 or less, 20 or less, or 15 or less.

(I) may be a polypeptide comprising ten or more consecutive amino acid residues in an amino acid sequence having one or more deletions, additions, substitutions or insertion in the amino acid sequence of SEQ ID NO:2 and capable of being used as the marker for determining the risk of developing the metabolic syndrome, and is preferably a polypeptide consisting of ten or more consecutive amino acid residues in an amino acid sequence having one or more deletions, additions, substitutions or insertion in the amino acid sequence of SEQ ID NO:2 and capable of being used as the marker for determining the risk of developing the metabolic syndrome.

(J) may be a polypeptide comprising ten or more consecutive amino acid residues in an amino acid sequence having 90% or more homology to the amino acid sequence of SEQ ID NO:2 and capable of being used as the marker for determining the risk of developing the metabolic syndrome, and is preferably a polypeptide consisting of ten or more consecutive amino acid residues in an amino acid sequence having 90% or more homology to the amino acid sequence of SEQ ID NO:2 and capable of being used as the marker for determining the risk of developing the metabolic syndrome.

One or several amino acid mutations in (I) is the same as those described for (B) in (1-1) above.

The homology in (J) is the same as that described for (C) in (1-1) above.

A peptide selected from the group consisting of (F) to (J) is preferably a peptide selected from the group consisting of (F-2) to (F-7), (G-2) to (G-7) and (H-2) to (H-7), more preferably a peptide of (F-6) or (F-7), and still more preferably a peptide of (F-7).

(2) Antibody or Aptamer of the Present Invention

The antibody or the aptamer of the present invention is an antibody or an aptamer that is bound to the marker peptide for determining the risk of developing the metabolic syndrome.

By the use of the antibody or the aptamer of the present invention, it is possible to measure an amount or the presence or absence of the marker peptide of the present invention for determining the risk of developing the metabolic syndrome, and is possible to determine the risk of developing the metabolic syndrome. That is, the risk of developing the metabolic syndrome is determined to be high if the amount of the marker peptide bound to the antibody or the aptamer when a biological sample collected from a subject is allowed to act upon the antibody or the aptamer of the present invention is higher than the amount of the marker peptide bound to the antibody or the aptamer when a biological sample collected from a healthy person is allowed to act upon the antibody or the aptamer of the present invention.

The antibody or the aptamer can be produced by standard methods.

An example in which the amount or the presence or absence of the marker peptide is measured using the antibody or the aptamer of the present invention will be shown below. First, the antibody or the aptamer is absorbed by a known method such as a physically absorption method or a covalent bond using functional groups to a carrier such as a microtiter plate. Subsequently, a biological sample is diluted as needed, added thereto, and incubated. Then, a secondary antibody conjugated to a fluorescence substance, a chemiluminescence substance or an enzyme is added, and the mixture is incubated. The reaction is detected by adding each substrate and subsequently measuring visible light due to fluorescence, chemiluminescence or an enzymatic reaction.

The marker peptide for determining the risk of developing the metabolic syndrome of the present invention is a peptide present at detectable level in a biological sample collected from a subject having the risk of developing the metabolic syndrome. Thus, the risk of developing the metabolic syndrome can be determined using the presence of the marker peptide of the present invention as an indicator.

(3) Microarray of the Present Invention

The microarray of the present invention is a microarray to which the antibody or the aptamer bound to the marker peptide for determining the risk of developing the metabolic syndrome described in the present invention has been immobilized.

The microarray collectively refers to a device in which a substance capable of being bound to a substance to be measured is aligned and immobilized on a carrier (substrate). A material for the carrier in the microarray may be any of an inorganic material such as glass or an organic material such as nitrocellulose. A shape of the carrier in the microarray may be any of a membrane, a bead or a plate.

The microarray of the present invention can be produced by immobilizing the antibody or the aptamer described in (2) above on the carrier. Instruments such as a microarrayer and a spotter can be used upon immobilization.

By the use of the microarray of the present invention, it is possible to measure the amount or the presence or absence of the marker peptide for determining the risk of developing the metabolic syndrome, and it is possible to determine the risk of developing the metabolic syndrome. That is, the risk of developing the metabolic syndrome is determined to be high if the amount of the marker peptide bound to the antibody or the aptamer on the microarray when a biological sample collected from a subject is allowed to act upon the microarray is higher than the amount of the marker peptide bound to the antibody or the aptamer on the microarray when a biological sample collected from a healthy person is allowed to act upon the microarray.

An example in which the amount of the marker peptide is measured using the microarray of the present invention will be shown below. First, a biological sample is added to the microarray on which the antibody or the aptamer has been immobilized, and the marker peptide in the biological sample is bound thereto. Subsequently, a secondary antibody conjugated to a fluorescence substance, a chemiluminescence substance or an enzyme is added, and the mixture is incubated. The reaction can be detected by adding each substrate and subsequently measuring visible light due to the fluorescence, the chemiluminescence or the enzymatic reaction.

(4) Determination Method of the Present Invention

The method for determining the risk of developing the metabolic syndrome of the present invention is a method for measuring the amount or the presence or absence of the marker peptide for determining the risk of developing the metabolic syndrome in a biological sample collected from a subject according to claim 1.

When the risk of developing the metabolic syndrome is determined by the amount of the marker peptide for determining the risk of developing the metabolic syndrome, the amount is generally compared with a reference value. Examples of the reference value may include an amount of the marker peptide in a biological sample collected from a healthy person (preferably has been surely confirmed to be the healthy person by a method other than the determination method of the present invention) and an amount of the marker peptide in a biological sample collected from a patient with metabolic syndrome (preferably has been surely confirmed to be the patient with metabolic syndrome by a method other than the determination method of the present invention). The former is preferable in these two.

When the reference value is the value from the healthy person, the risk of developing the metabolic syndrome is determined to be high when the amount of the marker peptide for determining the risk of developing the metabolic syndrome in the biological sample collected from the subject is higher than the amount of the marker peptide in the biological sample collected from the healthy person.

When the reference value is the value from the patient with metabolic syndrome, the risk of developing the metabolic syndrome is determined to be high when the amount of the marker peptide for determining the risk of developing the metabolic syndrome in the biological sample collected from the subject is equivalent to or higher than the amount of the marker peptide in the biological sample collected from the patient with metabolic syndrome.

In the determination method of the present invention, the risk of developing the metabolic syndrome is determined to be high when the amount of the marker peptide for determining the risk of developing the metabolic syndrome in the biological sample collected from the subject is higher than the amount of the marker peptide in the biological sample collected from the healthy person. On the other hand, the risk of developing the metabolic syndrome is determined to be low when the amount of the marker peptide for determining the risk of developing the metabolic syndrome in the biological sample collected from the subject is equivalent to or lower than the amount of the marker peptide in the biological sample collected from the healthy person.

Examples of the biological sample may include body fluids such as saliva, blood such as whole blood, plasma, and serum, urine and tear. Of these, the biological sample that is non-invasive and always collectable is preferable, and the saliva is more preferable. The saliva is also suitable as a specimen used for determination at home. Unstimulated saliva and stimulated saliva are available as a saliva specimen, and the stimulated saliva is preferable. The stimulated saliva can be collected easily by chewing a paraffin gum.

In the determination method of the present invention, the amount of the marker peptide for determining the risk of developing the metabolic syndrome can be measured by, for example, an immunoassay using the above antibody or aptamer, an immunoassay using the above microarray, a mass spectrometry, RIA (radioimmunoassay), ELISA (enzyme-linked immunosorbent assay), ECLIA (electrochemical luminescence immunoassay), or the like. The immunoassay using the antibody or the aptamer is as described in (2) above. The immunoassay using the microarray is as described in (3) above.

Various mass spectrometric apparatuses are available when the amount is measured by the mass spectrometry. Examples thereof may include GC-MS, LC-MS, FAB-MS, EI-MS, CI-MS, FD-MS, MALDI-MS, ESI-MS, HPLC-MS, FT-ICR-MS, CE-MS, ICP-MS, Py-MS, and TOF-MS, and any of them is available.

A multivariate analysis using amounts of two or more marker peptides for determining the risk of developing the metabolic syndrome as variables may be performed in the determination. Examples of the multivariate analysis may include a logistic regression analysis, a multi-regression analysis, a principal component analysis, an independent component analysis, a factor analysis, a discrimination analysis, a quantification theory, a cluster analysis, a conjoint analysis, and a multidimensional scaling method (MDS), and of these, the logistic regression analysis is preferable.

The marker peptide used in the determination method of the present invention may be one or more and may also be a combination of two or more. The combination of two or more is used when the multivariate analysis is performed. When two or more are combined, the number of the marker peptides may be 2, 3, 4, 5 or 6.

Examples of the preferable combination of the marker peptides may include the following combinations (1) to (3):

combination (1): one or more peptides selected from the group consisting of (A) to (E) and one or more peptides selected from the group consisting of (F) to (J);

combination (2): two or more peptides selected from the group consisting of (A) to (E); and combination (3): two or more peptides selected from the group consisting of (F) to (J).

The peptides selected from the group consisting of (A) to (E) and the peptides selected from the group consisting of (F) to (J) are as described in (1) above.

Preferable examples of the combination (1) may include the following combinations:

combination (1-1): combination of one or more peptides selected from the group consisting of (A-2) to (A-7), (B-2) to (B-7) and (C-2) to (C-7) with one or more peptides selected from the group consisting of (F-2) to (F-7), (G-2) to (G-7) and (H-2) to (H-7);

combination (1-2): combination of (A-6) and/or (A-7) with (F-6) and/or (F-7);

combination (1-3): combination of (A-7) with (F-7);

combination (1-4): combination of one or more peptides selected from the group consisting of (A-20) to (A-25), (B-20) to (B-25) and (C-20) to (C-25) with one or more peptides selected from the group consisting of (F-2) to (F-7), (G-2) to (G-7) and (H-2) to (H-7);

combination (1-5): combination of (A-24) and/or (A-25) with (F-6) and/or (F-7);

combination (1-6): combination of (A-25) with (F-7);

combination (1-7): combination of one or more peptides selected from the group consisting of (A-2) to (A-7), (B-2) to (B-7) and (C-2) to (C-7) and one or more peptides selected from the group consisting of (A-14) to (A-19), (B-14) to (B-19) and (C-14) to (C-19) and one or more peptides selected from the group consisting of (F-2) to (F-7), (G-2) to (G-7) and (H-2) and (H-7);

combination (1-8): combination of (A-6) and/or (A-7) and (A-18) and/or (A-19) and (F-6) and/or (F-7);

combination (1-9): combination of (A-7) and (A-19) and (F-7);

combination (1-10): combination of one or more peptides selected from the group consisting of (A-2) to (A-7), (B-2) to (B-7) and (C-2) to (C-7) and one or more peptides selected from the group consisting of (A-20) to (A-25), (B-20) to (B-25) and (C-20) to (C-25) and one or more peptides selected from the group consisting of (F-2) to (F-7), (G-2) to (G-7) and (H-2) to (H-7);

combination (1-11): combination of (A-6) and/or (A-7) and (A-24) and/or (A-25) and (F-6) and/or (F-7);

combination (1-12): combination of (A-7) and (A-25) and (F-7);

combination (1-13): combination of one or more peptides selected from the group consisting of (A-2) to (A-7), (B-2) to (B-7) and (C-2) to (C-7) and one or more peptides selected from the group consisting of (A-14) to (A-19), (B-14) to (B-19) and (C-14) to (C-19) and one or more peptides selected from the group consisting of (A-20) to (A-25), (B-20) to (B-25) and (C-20) to (C-25) and one or more peptides selected from the group consisting of (F-2) to (F-7), (G-2) to (G-7) and (H-2) to (H-7);

combination (1-14): combination of (A-6) and/or (A-7) and (A-18) and/or (A-19) and (A-24) and/or (A-25) and (F-6) and/or (F-7);

combination (1-15): combination of (A-7) and (A-19) and (A-25) and (F-7);

combination (1-16): combination of one or more peptides selected from the group consisting of (A-2) to (A-7), (B-2) to (B-7) and (C-2) to (C-7) and one or more peptides selected from the group consisting of (A-8) to (A-13), (B-8) to (B-13) and (C-8) to (C-13) and one or more peptides selected from the group consisting of (A-14) to (A-19), (B-14) to (B-19) and (C-14) to (C-19) and one or more peptides selected from the group consisting of (A-20) to (A-25), (B-20) to (B-25) and (C-20) to (C-25) and one or more peptides selected from the group consisting of (A-26) to (A-31), (B-26) to (B-31) and (C-26) to (C-31) and one or more peptides selected from the group consisting of (F-2) to (F-7), (G-2) to (G-7) and (H-2) to (H-7);

combination (1-17): combination of (A-6) and/or (A-7), (A-12) and/or (A-13), (A-18) and/or (A-19), (A-24) and/or (A-25), (A-30) and/or (A-31), and (F-6) and/or (F-7); and combination (1-18): combination of (A-7), (A-13), (A-19), (A-25), (A-31), and (F-7).

Examples of combination (2) may include the following combinations:

combination (2-1): combination of one or more peptides selected from the group consisting of (A-2) to (A-7), (B-2) to (B-7) and (C-2) to (C-7) with one or more peptides selected from the group consisting of (A-26) to (A-31), (B-26) to (B-31) and (C-26) to (C-31);

combination (2-2): combination of (A-6) and/or (A-7) with (A-30) and/or (A-31);

combination (2-3): combination of (A-7) with (A-31);

combination (2-4): combination of one or more peptides selected from the group consisting of (A-2) to (A-7), (B-2) to (B-7) and (C-2) to (C-7) and one or more peptides selected from the group consisting of (A-14) to (A-19), (B-14) to (B-19) and (C-14) to (C-19) and one or more peptides selected from the group consisting of (A-20) to (A-25), (B-20) to (B-25) and (C-20) to (C-25) and one or more peptides selected from the group consisting of (A-26) to (A-31), (B-26) to (B-31) and (C-26) to (C-31);

combination (2-5): combination of (A-6) and/or (A-7), (A-18) and/or (A-19), (A-24) and/or (A-25), and (A-30) and/or (A-31); and combination (2-6): combination of (A-7), (A-19), (A-25) and (A-31).

Among the combinations (1-1) to (1-18) and (2-1) to (2-6), the combinations (1-2), (1-3), (1-5), (1-6), (1-8), (1-9), (1-11), (1-12), (1-14), (1-15), (1-17), (1-18), (2-2), (2-3), (2-5), and (2-6) are preferable, and the combinations (1-3), (1-6), (1-9), (1-12), (1-15), (1-18), (2-3), and (2-6) are more preferable.

The determination method of the present invention is suitable for evaluating a physical constitution concerning predisposition for developing the metabolic syndrome in the subject. The determination method of the present invention can evaluate the presence or absence of the risk of developing the metabolic syndrome in the subject, and thus, can be used in preventive medicine. When a treatment or a preventive measure for the metabolic syndrome is given to the subject having the risk of developing the metabolic syndrome, the risk of developing the metabolic syndrome is reduced and the amount of the marker peptide is also decreased in response thereto. Therefore, the treatment or the preventive measure can be evaluated at the time of giving the treatment or the preventive measure, as well as measuring the amount or the presence or absence of the marker peptide. Therefore, the marker peptide of the present invention can becomes a biomarker for determining a therapeutic effect or a preventive effect such as a drug administration effect. Likewise, the determination method is also useful as a method for determining the therapeutic effect or the preventive effect such as an effect of administering a drug for the metabolic syndrome.

(5) Kit of the Present Invention

The kit for determining the risk of developing the metabolic syndrome of the present invention comprises the above antibody or aptamer, or the above microarray.

The kit of the present invention preferably further comprises a gum. This makes it easy to collect the stimulated saliva as a biological sample. The gum may be a gum such as paraffin gum generally used for collecting the stimulated saliva.

EXAMPLES

Example 1: Comparison of Amounts of P-B Peptide Fragment and GIRP Peptide Fragment Expressed in Saliva <Evaluation Method>
(1) Collection of Saliva Specimen Stimulated saliva (saliva obtained by promoting saliva secretion by chewing a paraffin gum) was collected from subjects having the following characteristics.

A (Healthy person group): male, abdominal girth of less than 85 cm, BMI of less than 25, not corresponding to any of the following (a) to (d) (n=10).

B (Obese person group): male, abdominal girth of 85 cm or more, or BMI of 25 or more, not corresponding to any of the following (a) to (d) (n=10).

C (Metabolic syndrome group): male, abdominal girth of 85 cm or more, or BMI of 25 or more, and corresponding to any one or more of the following (a) to (d) in blood examination (n=10).

Items:

(a) Neutral fat: 150 mg/dL or more, or HDL-cholesterol: 40 mg/dL or less;

(b) LDL-cholesterol: 140 mg/dL or more;

(c) Fasting blood sugar level: 110 mg/dL or more, or hemoglobin A1c: 5.8% or more; and (d) Uric acid: 7.0 mg/dL or more.

The subject belonging to the obese person group does not develop the metabolic syndrome, but is estimated to be highly likely to develop the metabolic syndrome.

(2) Comprehensive Analysis of Components in Saliva by Metabolome Analysis

The collected saliva was centrifuged to remove contaminants, and a supernatant was subjected to LC-MS (Positive/Negative), CE-MS (Anion/Cation). The saliva components were identified from Rt values and Ms values.

<Evaluation Results>

Figure 2:
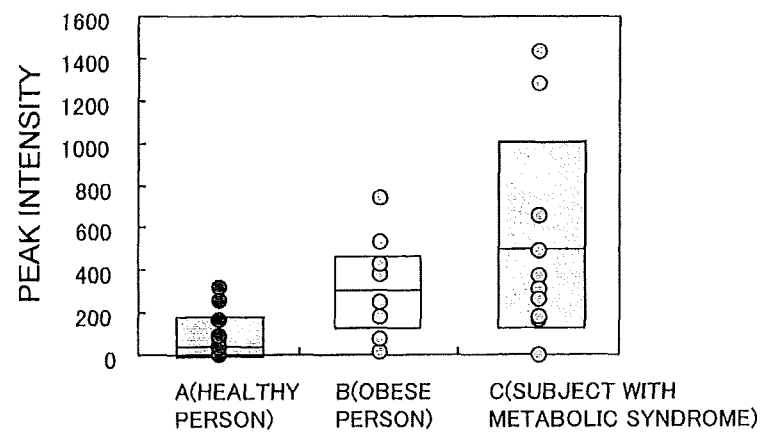
FIG. 2 is a graph showing a peak intensity of a GIPR peptide fragment in each subject group.

As a result of the saliva metabolome analysis, it was observed that a peak of a peptide (P-B peptide fragment $(1)^{27-54}$) consisting of amino acid residues at positions 27 to 54 in the amino acid sequence of SEQ ID NO:1 and a peak of a peptide consisting of amino acid residues at positions 264 to 275 in the amino acid sequence of SEQ ID NO:2 significantly increased in the metabolic syndrome group. As a result of database search for proteins, it was found that the amino acid sequence of SEQ ID NO:1 was an amino acid sequence of P-B peptide and the amino acid sequence of SEQ ID NO:2 was an amino acid sequence of GIPR and the above respective peptides were fragments thereof, respectively. A peak intensity in each subject group is shown in FIG. 1, FIG. 2, and Table 1. Results of significance tests for respective groups are shown in Table 2.

TABLE 1

PEAK INTENSITY OF P-B PEPTIDE FRAGMENT $(1)^{27-54}$ AND GIPR FRAGMENT IN EACH SUBJECT GROUP

| SUBJECT GROUP | PEAK INTENSITY OF P-B PEPTIDE $(1)^{27-54}$ | PEAK INTENSITY OF GIPR fragment |
|---|---|---|
| A (HEALTHY PERSON GROUP) | 4.4 | 98.7 |
| B (OBESE PERSON GROUP) | 52.0 | 328.1 |
| C (METABOLIC SYNDROME GROUP) | 46.9 | 516.8 |

TABLE 2

RESULTS OF SIGNIFICANT DIFFERENCE TESTS (TUKEY-
KRAMER TEST) FOR PEAK INTENSITY OF P-B PEPTIDE $(1)^{27-54}$
AND GIPR FRAGMENT BETWEEN EACH SUBJECT GROUP
AND HEALTHY PERSON GROUP

|  | PEAK INTENSITY OF P-B PEPTIDE $(1)^{27-54}$ | PEAK INTENSITY OF GIPR FRAGMENT |
|---|---|---|
| B (OBESE PERSON GROUP) | p < 0.05 | NO SIGNIFICANT DIFFERENCE |
| C (METABOLIC SYNDROME GROUP) | P < 0.05 | p < 0.05 |

As shown in FIG. 1, Table 1 and Table 2, the peak intensity of the P-B peptide fragment $(1)^{27-54}$ was significantly increased in the obese person group and the metabolic syndrome group compared with the healthy person group. This indicates that the risk of developing the metabolic syndrome can be determined to be high when the peak intensity of the P-B peptide fragment $(1)^{27-54}$ in the subject is higher than 4.4 that is the peak intensity in the healthy person group.

On the other hand, as shown in FIG. 2, Table 1 and Table 2, the peak intensity of the GIPR peptide fragment was not significantly different between the healthy person group and the obese person group, but was increased in the metabolic syndrome group with significant difference. This indicates that the risk of developing the metabolic syndrome can be determined to be high when the peak intensity of the GIPR peptide fragment in the subject is higher than 98.7 that is the peak intensity in the healthy person group.

Example 2: Determination of Metabolic Syndrome by Measuring Amount of P-B Peptide Fragment in Saliva Saliva samples were collected by the same technique as in Example 1 from 10 subjects corresponding to the metabolic syndrome group in the same criteria as in Example 1, and the peak intensity of the P-B peptide fragment $(1)^{27-54}$ was measured. As a result, the peak intensity of the P-B peptide fragment $(1)^{27-54}$ was higher than 4.4 in the saliva samples from 7 of the 10 subjects, and sensitivity for determining the metabolic syndrome was calculated to be 70%. This result indicates that the present invention is useful as a method for preliminarily determining the metabolic syndrome.

Example 3: Determination of Metabolic Syndrome by Measuring Amount of GIPR Peptide Fragment in Saliva Saliva samples were collected by the same technique as in Example 1 from 10 subjects corresponding to the metabolic syndrome group in the same criteria as in Example 1, and the peak intensity of the GIPR fragment was measured. As a result, the peak intensity of the peptide of SEQ ID NO:2 was higher than 98.7 in the saliva samples from 9 of the 10 subjects, and sensitivity for determining the metabolic syndrome was calculated to be 90%. This result indicates that the present invention is useful as the method for preliminarily determining the metabolic syndrome.

As described above, the metabolome analysis was performed for 40 saliva specimens from 10 healthy persons, 10 obese persons and 20 subjects having a metabolic syndrome tendency (10 subjects in Example 1 and 10 subjects in Examples 2 and 3), and the amounts of the P-B peptide fragment $(1)^{27-54}$ and the GIPR fragment significantly increased in the specimens from the group of the subjects having the metabolic syndrome tendency.

The above results indicate that the risk of developing the metabolic syndrome can be determined easily and accurately to some extent according to the present invention and the present invention is useful as the method for preliminarily determining the risk of developing the metabolic syndrome.

Example 4: Determination of Metabolic Syndrome by Measuring Amount of P-B Peptide Fragment in Saliva <Evaluation Method>

Forty saliva specimens were collected in the same manner as in Example 1 from 10 subjects corresponding to the healthy person group, 10 subjects corresponding to the obese person group and 20 subjects corresponding to the metabolic syndrome group (common to 20 subjects in Examples 1 to 3) on the same basis as in Example 1. The saliva metabolome analysis was performed for these saliva specimens in the same manner as in Example 1.

<Evaluation Results>

As a result of the saliva metabolome analysis, it was observed that peaks of the following four peptide fragments significantly increased in the metabolic syndrome group. The peak intensity in each subject group is shown in FIGS. 3 to 6 and Table 3.

P-B peptide fragment $(2)^{23-54}$: a peptide consisting of amino acid residues at positions 23 to 54 in the amino acid sequence of SEQ ID NO:1;

P-B peptide fragment $(3)^{55-79}$: a peptide consisting of amino acid residues at positions 55 to 79 in the amino acid sequence of SEQ ID NO:1;

P-B peptide fragment $(4)^{23-79}$: a peptide consisting of amino acid residues at positions 23 to 79 in the amino acid sequence of SEQ ID NO:1; and P-B peptide fragment $(5)^{23-35}$: a peptide consisting of amino acid residues at positions 23 to 35 in the amino acid sequence of SEQ ID NO:1.

TABLE 3

PEAK INTENSITY OF EACH P-B PEPTIDE FRAGMENT IN EACH SUBJECT GROUP

| | PEAK INTENSITY OF P-B PEPTIDE FRAGMENT (2)$^{23-54}$ | PEAK INTENSITY OF P-B PEPTIDE FRAGMENT (3)$^{55-79}$ | PEAK INTENSITY OF P-B PEPTIDE FRAGMENT (4)$^{23-79}$ | PEAK INTENSITY OF P-B PEPTIDE FRAGMENT (5)$^{23-35}$ |
|---|---|---|---|---|
| A (HEALTHY PERSON GROUP) | 0.0 | 228.2 | 85.9 | 28.8 |
| B (OBESE PERSON GROUP) | 8.9 | 431.5 | 128.5 | 85.3 |
| C (METABOLIC SYNDROME GROUP) | 24.35 | 421.05 | 431.75 | 180.75 |

Figure 3:
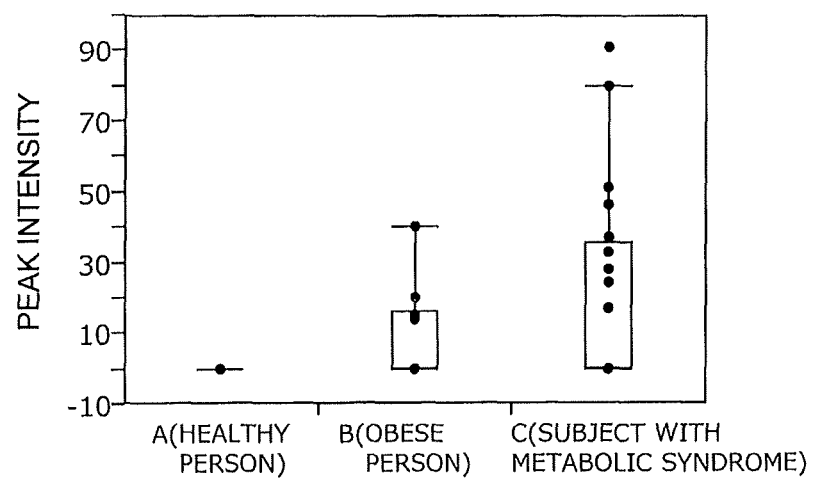
FIG. 3 is a graph showing a peak intensity of a P-B peptide fragment $(2)^{23-54}$ in each subject group.

As shown in FIG. 3 and Table 3, the peak intensity of the P-B peptide fragment (2)$^{23-54}$ increased compared with the peak intensity in the healthy person group. This indicates that the risk of developing the metabolic syndrome can be determined to be high when the peak intensity of the P-B peptide fragment (2)$^{23-54}$ in the subject is higher than 0.0 that is the peak intensity in the healthy person group.

Figure 4:
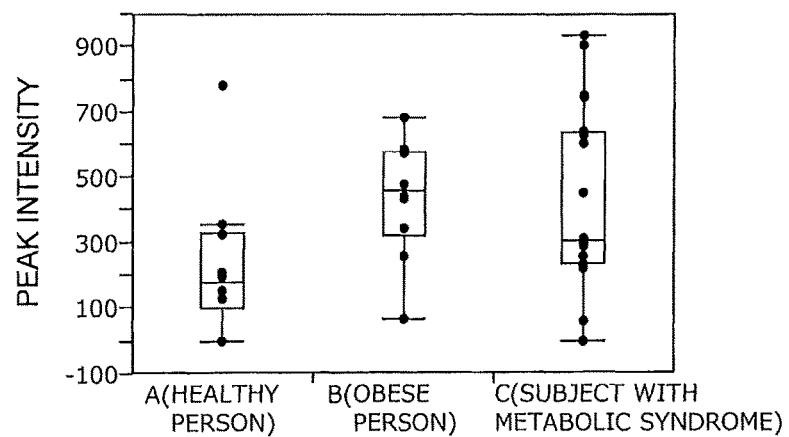
FIG. 4 is a graph showing a peak intensity of a P-B peptide fragment $(3)^{55-79}$ in each subject group.

As shown in FIG. 4 and Table 3, the peak intensity of the P-B peptide fragment (3)$^{55-79}$ increased compared with the peak intensity in the healthy person group. This indicates that the risk of developing the metabolic syndrome can be determined to be high when the peak intensity of the P-B peptide fragment (3)$^{55-79}$ in the subject is higher than 228.2 that is the peak intensity in the healthy person group.

Figure 5:
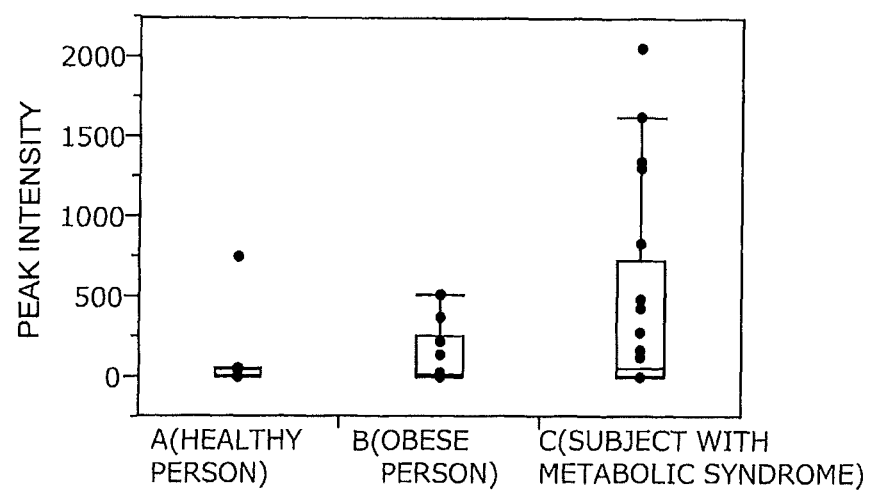
FIG. 5 is a graph showing a peak intensity of a P-B peptide fragment $(4)^{23-79}$ in each subject group.

As shown in FIG. 5 and Table 3, the peak intensity of the P-B peptide fragment (4)$^{23-79}$ increased compared with the peak intensity in the healthy person group. This indicates that the risk of developing the metabolic syndrome can be determined to be high when the peak intensity of the P-B peptide fragment (4)$^{23-79}$ in the subject is higher than 85.9 that is the peak intensity in the healthy person group.

Figure 6:
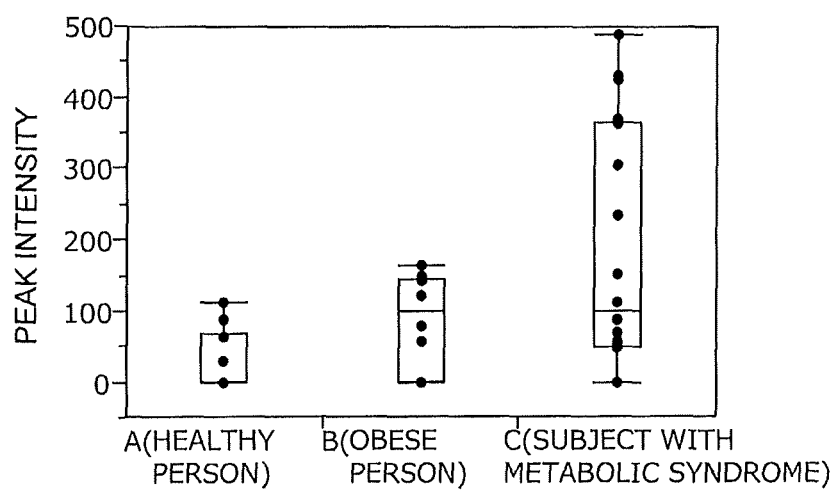
FIG. 6 is a graph showing a peak intensity of a P-B peptide fragment $(5)^{23-35}$ in each subject group.

As shown in FIG. 6 and Table 3, the peak intensity of the P-B peptide fragment (5)$^{23-35}$ increased compared with the peak intensity in the healthy person group. This indicates that the risk of developing the metabolic syndrome can be determined to be high when the peak intensity of the P-B peptide fragment (5)$^{23-35}$ in the subject is higher than 28.8 that is the peak intensity in the healthy person group.

Example 5: Enhancement of Diagnostic Accuracy by Multivariate Analysis (Logistic Regression Analysis) of Saliva Components A logistic regression analysis that is one of multivariate analyses was performed for five P-B peptide fragments and the GIPR fragment described in Examples 1 to 4 for the purpose of determining the metabolic syndrome with good accuracy. The logistic regression analysis is an analytical method commonly used when qualitative variables (whether the subject has developed the metabolic syndrome or not in this application) are predicted using a plurality of objective variables (saliva components in this application).

The logistic regression analysis was performed in combinations of the saliva components shown in Table 4 using the peak intensity obtained from the saliva specimens collected from 10 subjects in the healthy person group and 20 subjects in the metabolic syndrome group in Examples 1 to 4. Resulting parameter estimates (Table 5) were fitted to an equation 1, and a regression equation was calculated. A probability p that the subject was healthy was calculated by assigning each peak intensity obtained from the saliva specimens collected from 10 subjects in the healthy person group and 20 subjects in the metabolic syndrome group in Examples 1 to 3 in this regression equation. The subject was determined to be healthy in the case of p>0.5 or to have developed the metabolic syndrome in the case of p<0.5. A rate which was consistent with an actual result of determination was calculated as a rate of correct diagnosis (Table 6). As a result, it was suggested that the metabolic syndrome could be diagnosed with high accuracy by the use of the combination of the saliva components shown in Table 4.

TABLE 4

COMBINATION OF SALIVA COMPONENTS USED FOR LOGISTIC REGRESSION ANALYSIS.

| COMBINATION | P-B PEPTIDE FRAGMENT (1)$^{27-54}$ | P-B PEPTIDE FRAGMENT (2)$^{23-54}$ | P-B PEPTIDE FRAGMENT (3)$^{55-79}$ | P-B PEPTIDE FRAGMENT (4)$^{23-79}$ | P-B PEPTIDE FRAGMENT (5)$^{23-35}$ | GIPR FRAGMENT |
|---|---|---|---|---|---|---|
| 1 | ○ | — | — | — | — | ○ |
| 2 | — | — | — | ○ | — | ○ |
| 3 | ○ | — | — | — | ○ | — |
| 4 | ○ | — | ○ | — | — | ○ |
| 5 | ○ | — | — | ○ | — | ○ |
| 6 | ○ | — | ○ | ○ | — | ○ |
| 7 | ○ | — | ○ | ○ | ○ | — |
| 8 | ○ | ○ | ○ | ○ | ○ | ○ |

TABLE 5

PARAMETER ESTIMATES IN LOGISTIC REGRESSION ANALYSIS

| COMBI-NATION | $b_0$ | $b_1$ | $b_2$ | $b_3$ | $b_4$ | $b_5$ | $b_6$ |
|---|---|---|---|---|---|---|---|
| 1 | 1.95779 | −0.07427 | — | — | — | — | −0.00611 |
| 2 | 1.18868 | — | — | — | 0.00405 | — | −0.01178 |
| 3 | 1.30377 | −0.07372 | — | — | — | −0.00945 | — |
| 4 | 1.34752 | −0.12465 | — | 0.00523 | — | — | −0.00750 |
| 5 | 2.46830 | −0.07615 | — | — | 0.00571 | — | −0.01186 |
| 6 | 1.66504 | −0.26988 | — | 0.01437 | 0.00971 | — | −0.01958 |
| 7 | 0.70607 | −0.15464 | — | 0.00610 | 0.00437 | −0.02409 | — |
| 8 | 1.16891 | −0.26249 | −4.36836 | 0.01724 | 0.11165 | −0.01282 | −0.02278 |

[Mathematical 1]

$$p = \frac{1}{1 + \exp[-(b_0 + b_1x_1 + b_2x_2 + b_3x_3 + b_4x_4 + b_5x_5 + b_6x_6)]} \quad \langle \text{EQUATION 1}\rangle$$

Explanation for Equation 1
x1: Peak intensity of P-B peptide fragment $(1)^{27-54}$
x2: Peak intensity of P-B peptide fragment $(2)^{23-54}$
x3: Peak intensity of P-B peptide fragment $(3)^{55-79}$
x4: Peak intensity of P-B peptide fragment $(4)^{23-79}$
x5: Peak intensity of P-B peptide fragment $(5)^{23-35}$
x6: Peak intensity of GIPR fragment

TABLE 6

TRUE POSITIVE RATE OBTAINED BY EACH COMBINATION OF SALIVA COMPONENTS

| COMBINATION | RATE Of CORRECT DIAGNOSIS |
|---|---|
| 1 | 86.7% |
| 2 | 83.3% |
| 3 | 83.3% |
| 4 | 90.0% |
| 5 | 86.7% |
| 6 | 93.3% |
| 7 | 86.7% |
| 8 | 96.7% |

An area under an ROC (receiver operating characteristic) curve was calculated in order to compare a diagnostic capability when the combination of these saliva components was used with a diagnostic capability when a single saliva component descried in Examples 1 to 3 was used. A plurality of cutoff values for discriminating the healthy persons from the subjects with metabolic syndrome was configured, and each sensitivity and specificity degree were calculated. The sensitivity and [1-Specificity degree] were plotted on a vertical axis and an abscissa axis, respectively to depict an ROC curve. The larger the area under this ROC curve is, the higher the diagnostic capability is determined to be ("Easy-to-Follow Medical Statistics" written by Toshio Morizane, p. 254, published by Medical Tribune Inc.). As a result, as shown in Table 7, it was suggested that the diagnostic capability was enhanced by the combination of the saliva components compared with the case of using the single saliva component.

TABLE 7

AREA UNDER ROC CURVE BY SALIVA COMPONENT(s) (SINGLE AND COMBINATION)

| SALIVA COMPONENTS AND COMBINATIONS | | AREA UNDER ROC CURVE |
|---|---|---|
| P-B PEPTIDE FRAGMENT $(1)^{27-54}$ | | 0.8375 |
| P-B PEPTIDE FRAGMENT $(2)^{23-54}$ | | 0.7250 |
| P-B PEPTIDE FRAGMENT $(3)^{55-79}$ | | 0.7150 |
| P-B PEPTIDE FRAGMENT $(4)^{23-79}$ | | 0.6500 |
| P-B PEPTIDE FRAGMENT $(5)^{23-35}$ | | 0.7800 |
| GIPR FRAGMENT | | 0.8475 |
| COMBINATION | 1 | 0.9275 |
| | 2 | 0.8675 |
| | 3 | 0.8875 |
| | 4 | 0.9450 |
| | 5 | 0.9425 |
| | 6 | 0.9700 |
| | 7 | 0.9050 |
| | 8 | 0.9800 |

The invention claimed is:

1. A method of detecting a level of at least one peptide with a minimum length of 10 amino acids of amino acids 23 to 79 of SEQ ID NO:1, the method comprising
measuring the level of the at least one peptide in a sample obtained from a subject,
wherein the level of the at least one peptide is measured by mass spectrometry, an immunoassay using an antibody or an aptamer which binds to the at least one peptide or an immunoassay using the microarray in which an antibody or an aptamer which binds to the at least one peptide has been is immobilized to a carrier.

2. The method according to claim 1, comprising measuring two or more peptides.

3. The method according to claim 1, wherein the sample is a saliva sample.

4. The method of claim 1, wherein the subject is human.

5. The method of claim 1, wherein the at least one peptide is selected from the group consisting of a peptide with 10 or more amino acids of amino acids 27 to 54 of SEQ ID NO:1, a peptide with 10 or more amino acids of amino acids 23 to 54 of SEQ ID NO:1, 10 or more amino acids of amino acids 55 to 79 of SEQ ID NO:1, and a peptide with 10 or more amino acids of amino acids 23 to 35 of SEQ ID NO:1.

6. The method of claim 1, wherein the at least one peptide has a minimum length of 13 amino acid residues.

7. The method of claim 5, wherein the at least one peptide is a peptide with 10 or more amino acids of amino acids 27 to 54 of SEQ ID NO:1.

8. The method of claim 5, wherein the at least one peptide is a peptide with 10 or more amino acids of amino acids 23 to 54 of SEQ ID NO:1.

9. The method of claim 5, wherein the at least one peptide is a peptide with 10 or more amino acids of amino acids 55 to 79 of SEQ ID NO:1.

10. The method of claim 5, wherein the at least one peptide is a peptide with 10 or more amino acids of amino acids 23 to 35 of SEQ ID NO:1.

* * * * *